United States Patent [19]

Masaki et al.

[11] Patent Number: 5,250,546
[45] Date of Patent: Oct. 5, 1993

[54] AMINO-ALCOHOL DERIVATIVES AND PROCESSES FOR THEIR PREPARATION

[75] Inventors: Mitsuo Masaki, Chiba; Haruhiko Shinozaki, Omiya; Masaru Satoh, Koshigaya; Naoya Moritoh, Kuki; Koichi Hashimoto; Toshiro Kamishiro, both of Misato, all of Japan

[73] Assignee: Nippon Chemiphar Co., Ltd., Tokyo, Japan

[21] Appl. No.: 551,037

[22] Filed: Jul. 11, 1990

Related U.S. Application Data

[63] Continuation of Ser. No. 191,743, May 6, 1988, abandoned, which is a continuation of Ser. No. 778,967, Sep. 23, 1985, abandoned.

[30] Foreign Application Priority Data

Sep. 28, 1984 [JP]   Japan ................. 59-203623

[51] Int. Cl.$^5$ .......................................... A61K 41/445
[52] U.S. Cl. ..................... 514/331; 514/212;
514/237.8; 514/238.8; 514/374; 514/378;
514/428; 514/653; 540/609; 544/88; 544/98;
544/106; 544/162; 546/232; 546/216; 548/215;
548/235; 548/237; 548/240; 548/247; 548/560;
548/561; 548/562
[58] Field of Search ............... 564/355, 364; 514/653,
514/331, 649, 650; 546/192, 232, 544; 540/609;
544/88, 98, 106, 162; 548/215, 235, 237, 240,
247, 560, 561, 562, 564

[56] References Cited

U.S. PATENT DOCUMENTS

| | | | |
|---|---|---|---|
| Re. 27,822 | 11/1973 | Koppe et al. ................. | 564/345 X |
| 2,046,946 | 7/1936 | Heilrer et al. ................. | 260/128.5 |
| 2,046,947 | 7/1936 | Heilrer et al. ................. | 260/128.5 |
| 3,153,093 | 10/1964 | Horrom et al. ................. | 564/367 |
| 3,536,712 | 10/1970 | Keck et al. ................. | 564/364 X |
| 3,574,211 | 4/1971 | Keck et al. ................. | 564/363 |
| 3,590,084 | 6/1971 | Peperkamp et al. ............. | 260/570.7 |
| 3,644,353 | 2/1972 | Lunts et al. ................. | 564/365 X |
| 3,644,520 | 2/1972 | Hartley et al. ................. | 564/365 X |
| 3,694,138 | 9/1972 | Kalopissis et al. ............. | 564/367 X |
| 3,728,346 | 4/1973 | Klinger ................. | 564/364 X |
| 3,928,603 | 12/1975 | Moreau et al. ................. | 564/367 X |
| 3,933,913 | 1/1976 | Colella et al. ................. | 564/367 X |
| 3,954,871 | 5/1976 | Buu-Hoi et al. ................. | 260/570.6 |
| 3,966,814 | 6/1976 | Schromm et al. ............... | 564/358 X |
| 4,282,251 | 8/1981 | Berney ................. | 564/365 X |
| 4,652,584 | 3/1987 | Carsan ................. | 514/524 |

OTHER PUBLICATIONS

J. C. Watkins, "Structure-activity studies on mammalian glutamate receptors", *Molecular Basis of Drug & Pesticide Action, Neurotox '88*, pp. 445-449, G. G. Lunt, Editor (1988).

*Primary Examiner*—Glennon H. Hollrah
*Assistant Examiner*—Brian M. Burn
*Attorney, Agent, or Firm*—Oblon, Spivak, McClelland, Maier & Neustadt

[57] ABSTRACT

Amino-alcohol derivatives of the formula, $$\underset{X}{\underset{|}{\bigcirc}}-\underset{R_1}{\overset{OR_4}{\underset{|}{CH}}}-\overset{R_5}{\underset{|}{CH}}-N-(CH_2)_n-N\diagup_{R_3}^{R_2}$$

where $R_1$ is a straight or branched alky group having 3 to 8 carbon atoms, $R_2$ and $R_3$ are each a lower alkyl group, or $R_2$ and $R_3$ form a 5- to 7-membered ring together with the adjacent nitrogen atom which may have an oxygen atom attached thereto, $R_4$ is a hydrogen atom or a lower alkyl group, $R_5$ is a hydrogen atom or a lower alkyl group, X is a hydrogen or halogen atom or a lower alkyl or lower alkoxy group, and n is an integer of 2 or 3, and acid addition salts thereof, are effectively useful as medicines and agricultural chemicals. Processes are also disclosed for preparing such compounds.

48 Claims, No Drawings

AMINO-ALCOHOL DERIVATIVES AND PROCESSES FOR THEIR PREPARATION

This application is a continuation of application Ser. No. 07/191,743, filed on May 6, 1988, now abandoned, which is a continuation of application Ser. No. 06/778,967, filed Sep. 23, 1985, abandoned.

BACKGROUND OF THE INVENTION

1. Field of the Invention

This invention relates to novel amino-alcohol derivatives and more particularly to amino-alcohol derivatives of the formula (I),

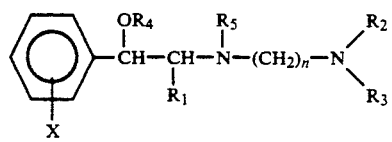

where $R_1$ is a straight or branched alkyl group having 3 to 8 carbon atoms, $R_2$ and $R_3$ are each a lower alkyl group, or $R_2$ and $R_3$ form a 5- to 7-membered ring together with the adjacent nitrogen atom which may have an oxygen atom attached thereto, $R_4$ is a hydrogen atom or a lower alkyl group, $R_5$ is a hydrogen atom or a lower alkyl group, X is a hydrogen or halogen atom or a lower alkyl or lower alkoxy group, and n is an integer of 2 or 3, or acid addition salts thereof. The invention further relates to processes for preparing these compounds.

2. Description of the Prior Art

As has been strongly suggested in the art, glutamic acid acts as an excitatory neurotransmitter at the central nervous systems of higher animals and at the neuromuscular junctions of lower animals ["Glutamate as a Neurotransmitter" edited by G. D. Chiara & G. L. Gessa: Raven Press, New York, 1981 and H. M. Gerschenfeld: Physiol. Rev., 53, 1-119 (1973)]. It has also been reported that dystropy, rigidity, tremors, convulsions and the like are induced by the administration of kainic acid, domoic acid, quisqualic acid, ibotenic acid or the like, which acids are extremely strong agonists for glutamic acid in higher animals [Oleny et al.: Brain Res., 77, 507-512 (1974)].

It is known that as aging proceeds, the central and peripheral nervous systems would undergo hypoergia to develop Parkinson's disease, motoneuron disorders, dementia, tremors, spinocerebellar degeneracy and the like. These diseases are considered to be attributable to off-balanced equilibration between excitatory nerves and inhibitory nerves (for example, the equilibration between glutamic acid and GABA) due to loss of neurons at certain specific sites or overall hypoergia of the nervous systems [Toshishige Hirai: Shinkei Shimpo, 17, 69 (1973)].

With the foregoing in view, medicines that can selectively block glutamic acid are useful for the therapy of neuropathy from which the senile would most often suffer and which would involve such complaints as vertigo, shoulder discomfort, convulsions, tremors and the like, all of them resulting from off-balanced nervous systems or hyperstenia in muscle discharge.

Glutamic acid also acts as an excitatory neurotransmitter for neuromuscular junctions of insects. Chemicals capable of blocking glutamic acid are therefore suitable for agricultural use for their ability to reduce and weaken insects' activities [Morifusa Eto: Kagaku to Seibutsu, 21, 725 (1983)].

It has now been found that amino-alcohol derivatives of the formula (I) above have excellent blocking effects against glutamic acid as well as neuraxial muscle relaxing effects, i.e. rigidity reducing and releasing effects on anemic decerebrate rigidity samples.

This result suggests that the inventive compounds are useful for the therapy of a complaint which would have spastic paralysis and rigidity and these compounds are expected to suppress or release dyskinasis, athetosis, myoclonus, tic, tremors, dystonia and ballismus of neuropathy.

Some compounds are known which are structurally similar to the compounds contemplated by the present invention. Such known compounds are 2-(2-dimethylaminoethylamino)-1-phenylpropan-1-ol [Sv. Zikolova and L. Zhelyazkov: Tr. Nauchno-Izsled. Inst. Farm., 3, 14-19 (1961) (CA, 61, 9485b)], 1-phenyl-2-(2-piperidinoethylamino)propan-1-ol and 1-phenyl-2-(2-pyrrolidinoethylamino)propan-1-ol [ibid., L. Zhelyazkov, A. Georgiev, Sv. Zikolova, P. Manolov, L Daleva and M. Kazandzhiev: Tr. Nauchnoizsled. Khim.-Farm. Inst., 1972, 7, 33-53 (CA, 79, 27099g) and L. Daleva, P. Manolov: Tr. Nauchnoizsled. Khim.-Farm. Inst., 1972, 7, 229-240 (CA, 79, 27213g)]and 2-(2-morpholinoethylamino)-1-phenylpropan-1-ol [Sv. Zikolova and L. Zhelyazkov: Farmatsiya, 14, (5), 16-21 (1964) (CA, 62, 13135g)]. These prior art publications however are silent as to whether the known compounds would have blocking effects against glutamic acid. Experiments conducted by the present inventors show that those compounds are only marginal in their glutamic acid blocking effects and in their rigidity reducing and releasing effects as compared with the compounds of the invention.

SUMMARY OF THE INVENTION

It is an object of the present invention to provide novel amino-alcohol derivatives of the formula (I) above which have excellent blocking effects against glutamic acid and rigidity reducing and releasing effects and hence are effectively useful as medicines and agricultural chemicals.

Another object of the invention is to provide processes for preparing such compounds.

These and other objects and features of the invention can be attained by the provision of an amino-alcohol derivative of the formula (I),

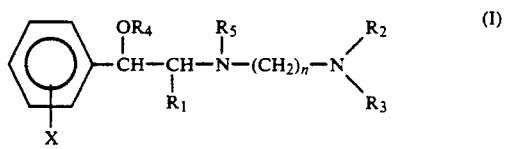

where $R_1$ is a straight or branched alkyl group having 3 to 8 carbon atoms, $R_2$ and $R_3$ are each a lower alkyl group, or $R_2$ and $R_3$ form a 5- to 7-membered ring together with the adjacent nitrogen atom which may have an oxygen atom attached thereto, $R_4$ is a hydrogen atom or a lower alkyl group, $R_5$ is a hydrogen atom or a lower alkyl group, X is a hydrogen or halogen atom or a lower alkyl or lower alkoxy group, n is an integer of 2 or 3, or an acid addition salt thereof.

DETAILED DESCRIPTION OF THE INVENTION

Amino-alcohol derivatives of the present invention contain two types of compounds, i.e. a compound of the formula (Ia) and a compound of the formula (Ib),

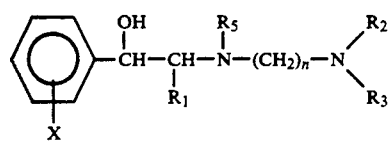

(Ia)

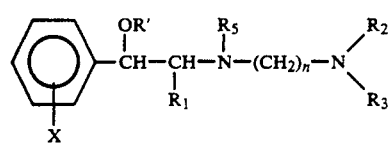

(Ib)

where R' is a lower alkyl group, and $R_1$, $R_2$, $R_3$, $R_5$, X and n are as defined previously.

Both of these compounds of the invention can be prepared, for example, by one of the following processes.

Process 1

In accordance with the following reaction scheme, a compound of the formula (II) is reacted with a compound of the formula (III) to prepare the desired compound (Ia),

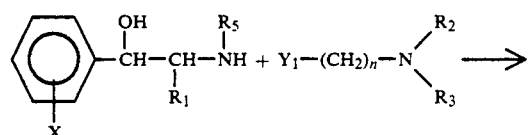

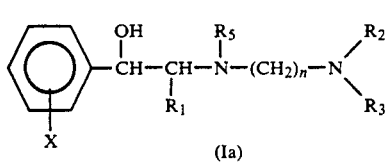

(Ia)

where $Y_1$ is a halogen atom or a tosyloxy group, and $R_1$, $R_2$, $R_3$, $R_5$, X and n are as defined previously.

The reaction of the compound (II) with the compound (III) is effected at 50° to 150° C. This reaction may be conducted without a solvent under normal conditions, but it is possible to use an inert solvent.

Process 2

In accordance with the following reaction scheme, the compound (Ia) is reacted with a compound of the formula (IV) to prepare the desired compound (Ib),

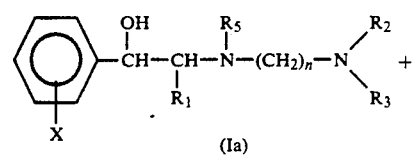

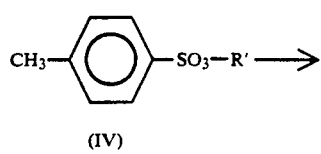

(IV)

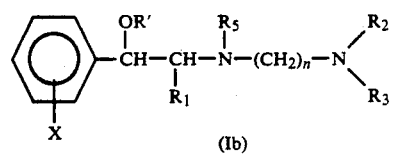

(Ib)

R' is a lower alkyl group, and $R_1$, $R_2$, $R_3$, $R_5$, X and n are as defined previously.

This reaction is conducted by reacting an alcoholate anion of the compound (Ia) with the compound (IV). The alcoholate is obtained by treating the compound (Ia) with a base such as sodium hydride in an organic solvent such as benzene or toluene at room temperature to 150° C.

Process 3

In accordance with the following reaction scheme, a desired compound of the formula (Ia') is obtained by reducing a compound of the formula (V),

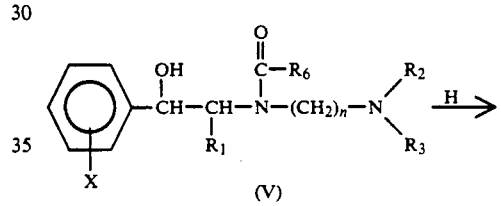

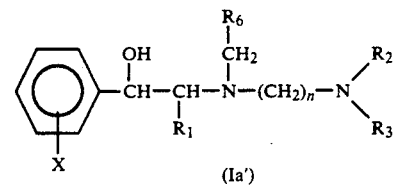

(Ia')

where $R_6$ is a hydrogen atom or a lower alkyl group, and $R_1$, $R_2$, $R_3$, X and n are as defined previously.

The compound (V) which is a starting material for this reaction is obtained by acylating a compound of the formula (Ia"),

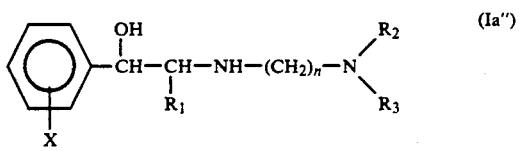

(Ia")

where $R_1$, $R_2$, $R_3$, X and n are as defined previously.

The reaction is effected with use of a reducing agent such as lithium aluminum hydride in a solvent such as tetrahydrofuran or ether at 0° C. to the boiling point of the solvent.

Process 4

In accordance with the following reaction scheme, a compound of the formula (VI) is reacted with a compound of the formula (VII) to prepare a desired compound of the formula (I),

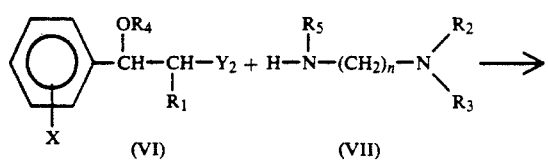

(VI)  (VII)

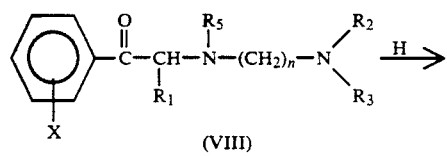

(I)

where $Y_2$ is a halogen atom, and $R_1$, $R_2$, $R_3$, $R_4$, $R_5$, X and n are as defined previously.

The reaction of the compound (VI) with the compound (VII) is effected with or without a solvent at 50° to 150° C. for 1 to 10 hours.

Process 5

In accordance with the following reaction scheme, the desired compound (Ia) is obtained by reducing a compound of the formula (VIII),

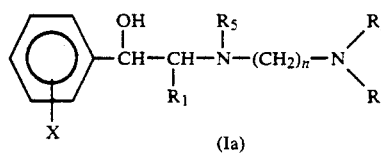

(VIII)

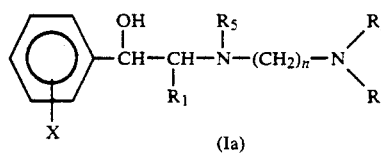

(Ia)

where $R_1$, $R_2$, $R_3$, $R_5$, X and n are as defined previously.

The reduction is effected in the usual manner. For example, the following reaction techniques may be employed.

1) Hydrogenation in the presence of a catalyst such as Raney-nickel, platinum, palladium-carbon or the like in a solvent such as methanol or ethanol
2) Reduction using a metal hydride complex, for example, sodium borohydride in a solvent such as methanol or ethanol, or lithium aluminum hydride in an organic solvent such as ether or tetrahydrofuran
3) Reduction using an aluminum alkoxide such as aluminum isopropoxide in an organic solvent such as isopropanol or the like Process 6

In accordance with the following reaction scheme, the desired compound (I) is obtained by reacting a compound of the formula (IX) with the compound (VII) under reducing conditions,

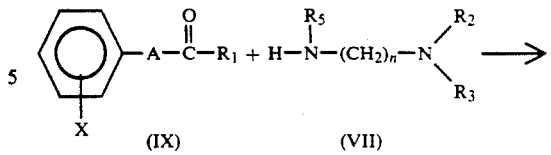

(IX)  (VII)

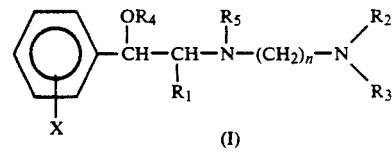

(I)

where A is

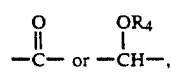

and $R_1$, $R_2$, $R_3$, $R_4$, $R_5$, X and n are as defined previously.

In the case where A is

the reaction is effected in the presence of zinc and sulfurous acid in a solvent such as methanol or ethanol at 50° to 150° C. for 0.5 to 5 hours. In the case where A is

the reaction is effected by hydrogenation in the presence of a catalyst such as Raney-nickel, platinum, palladium-carbon or the like in a solvent such as methanol or ethanol, or by reduction using a metal hydride complex, for example, sodium cyanoborohydride in a solvent such as methanol or ethanol, preferably in a pH range of 6 to 9, or sodium borohydride in the presence of acetic acid and sodium acetate in a solvent such as alcohol-containing water.

Process 7

In accordance with the following reaction scheme, a desired compound of the formula (Ia″) is obtained by hydrolyzing a compound of the formula (X),

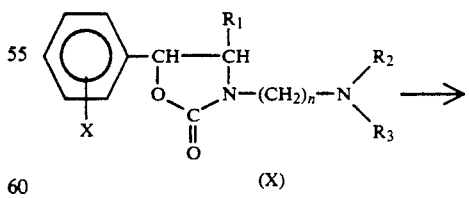

(X)

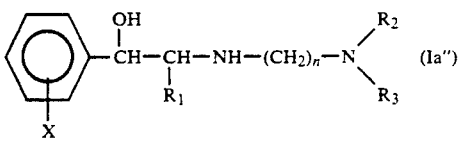

(Ia″)

where $R_1$, $R_2$, $R_3$, X and n are as defined previously.

This reaction is effected by hydrolyzing the compound (X) in the presence of a base such as sodium hydroxide in alcohol-containing water at 50° to 100° C.

The amino-alcohol derivatives (I) thus prepared can be converted in conventional manner to their acid addition salts. Acid addition salts useful in the invention include, for example, hydrochlorides, hydrobromides, phosphates, sulfates, p-toluene-sulfonates, fumarates, citrates, maleates, tartrates and the like.

Each of the compounds contemplated by the present invention includes its stereoisomers, i.e. an erythro form (1RS,2SR) and a threo form (1RS,2RS), and its optical isomers (1R,2S), (1S,2R), (1R,2R) and (1S,2S). It is to be noted that these two types of isomers are within the scope of the invention.

The following compounds are particularly typical of the compounds (I) of the present invention.

Compound 1 : (1RS,2SR)-1-phenyl-2-(3-piperidinopropylamino)pentan-1-ol dihydrochloride
Compound 2 : (1RS,2RS)-1-phenyl-2-(3-piperidinopropylamino)pentan-1-ol dihydrochloride
Compound 3 : (1RS,2SR)-1-phenyl-2-(3-piperidinopropylamino)hexan-1-ol dihydrochloride
Compound 4 : (1RS,2RS)-1-phenyl-2-(3-piperidinopropylamino)hexan-1-ol dihydrochloride
Compound 5 : (1RS,2SR)-1-phenyl-2-(3-piperidinopropylamino)heptan-1-ol dihydrochloride
Compound 6 : (1RS,2RS)-1-phenyl-2-(3-piperidinopropylamino)heptan-1-ol dihydrochloride
Compound 7 : (1RS,2SR)-1-phenyl-2-(3-piperidinopropylamino)octan-1-ol dihydrochloride
Compound 8 : (1RS,2RS)-1-phenyl-2-(3-piperidinopropylamino)octan- 1-ol dihydrochloride
Compound 9 : (1RS,2SR)-1-phenyl-2-(3-piperidinopropylamino)nonan-1-ol dihydrochloride
Compound 10: (1RS,2RS)-1-phenyl-2-(3-piperidinopropylamino)nonan-1-ol dihydrochloride
Compound 11: (1RS,2SR)-1-phenyl-2-(3-piperidinopropylamino)decan-1-ol dihydrochloride
Compound 12: (1RS,2RS)-1-phenyl-2-(3-piperidinopropylamino)decan-1-ol dihydrochloride
Compound 13: (1RS,2SR)-3-methyl-1-phenyl-2-(3-piperidinopropylamino)butan-1-ol dihydrochloride
Compound 14: (1RS,2RS)-3-methyl-1-phenyl-2-(3-piperidinopropylamino)butan-1-ol dihydrochloride
Compound 15: (1RS,2SR)-4-methyl-1-phenyl-2-(3-piperidinopropylamino)pentan-1-ol dihydrochloride
Compound 16: (1RS,2RS)-4-methyl-1-phenyl-2-(3-piperidinopropylamino)pentan-1-ol dihydrochloride
Compound 17: (1R,2S)-4-methyl-1-phenyl-2-(3-piperidinopropylamino)pentan-1-ol dihydrochloride
Compound 18: (1S,2R)-4-methyl-1-phenyl-2-(3-piperidinopropylamino)pentan-1-ol dihydrochloride
Compound 19: (1S,2S)-4-methyl-1-phenyl-2-(3-piperidinopropylamino)pentan-1-ol dihydrochloride
Compound 20: (1R,2R)-4-methyl-1-phenyl-2-(3-piperidinopropylamino)pentan-1-ol dihydrochloride
Compound 21: (1RS,2SR)-5-methyl-1-phenyl-2-(3-piperidinopropylamino)hexan-1-ol dihydrochloride
Compound 22: (1RS,2RS)-5-methyl-1-phenyl-2-(3-piperidinopropylamino)hexan-1-ol dihydrochloride
Compound 23: (1RS,2SR)-4-methyl-1-phenyl-2-(3-pyrrolidinopropylamino)pentan-1-ol dihydrochloride
Compound 24: -methyl-1-phenyl-2-(3-pyrrolidinopropylamino)pentan-1-ol dihydrochloride
Compound 25: (1RS,2SR)-4-methyl-2-(3-morpholinopropylamino)-1-phenylpentan-1-ol dihydrochloride
Compound 26: (1RS,2RS)-4-methyl-2-(3-morpholinopropylamino)-1-phenylpentan-1-ol dihydrochloride
Compound 27: (1RS,2SR)-2-(3-dimethylaminopropylamino)-4-methyl-1-phenylpentan-1-ol dihydrochloride
Compound 28: (1RS,2RS)-2-(3-dimethylaminopropylamino)-4-methyl-1-phenylpentan-1-ol dihydrochloride
Compound 29: (1RS,2SR)-4-methyl-1-phenyl-2-(2-piperidinoethylamino)pentan-1-ol dihydrochloride
Compound 30: (1RS,2RS)-4-methyl-1-phenyl-2-(2-piperidinoethylamino)pentan-1-ol dihydrochloride
Compound 31: (1RS,2SR)-4-methyl-1-phenyl-2-(2-pyrrolidinoethylamino)pentan-1-ol dihydrochloride
Compound 32: (1RS,2RS)-4-methyl-1-phenyl-2-(2-pyrrolidinoethylamino)pentan-1-ol dihydrochloride
Compound 33: (1RS,2SR)-4-methyl-2-[3-(perhydroazepin-1-yl)propylamino]-1-phenylpentan-1-ol dihydrochloride
Compound 34: (1RS,2RS)-4-methyl-2-[3-(perhydroazepin-1-yl)propylamino]-1-phenylpentan-1-ol dihydrochloride
Compound 35: (1RS,2SR)-5-methyl-1-phenyl-2-(3-pyrrolidinopropylamino)hexan-1-ol dihydrochloride
Compound 36: (1RS,2RS)-5-methyl-1-phenyl-2-(3-pyrrolidinopropylamino)hexan-1-ol dihydrochloride
Compound 37: (1RS,2SR)-5-methyl-2-(3-morpholinopropylamino)-1-phenylhexan-1-ol dihydrochloride
Compound 38: (1RS,2RS)-5-methyl-2-(3-morpholinopropylamino)-1-phenylhexan-1-ol dihydrochloride
Compound 39: (1RS,2SR)-2-(3-dimethylaminopropylamino)-5-methyl-1-phenylhexan-1-ol dihydrochloride
Compound 40: (1RS,2RS)-2-(3-dimethylaminopropylamino)-5-methyl-1-phenylhexan-1-ol dihydrochloride
Compound 41: (1RS,2SR)-5-methyl-1-phenyl-2-(2-piperidinoethylamino)hexan-1-ol dihydrochloride
Compound 42: (1RS,2RS)-5-methyl-1-phenyl-2-(2-piperidinoethylamino)hexan-1-ol dihydrochloride
Compound 43: (1RS,2SR)-5-methyl-1-phenyl-2-(2-pyrrolidinoethylamino)hexan-1-ol dihydrochloride
Compound 44: (1RS,2RS)-5-methyl-1-phenyl-2-(2-pyrrolidinoethylamino)hexan-1-ol dihydrochloride
Compound 45: (1RS,2SR)-5-methyl-2-[3-(perhydroazepin-1-yl)propylamino]-1-phenylhexan-1-ol dihydrochloride
Compound 46: (1RS,2RS)-5-methyl-2-[3-(perhydroazepin-1-yl)propylamino]-1-phenylhexan-1-ol dihydrochloride
Compound 47: (1RS,2SR)-4-methyl-1-(2-methylphenyl)-2-(3-piperidinopropylamino)pentan-1-ol dihydrochloride
Compound 48: (1RS,2RS)-4-methyl-1-(2-methylphenyl)-2-(3-piperidinopropylamino)pentan-1-ol dihydrochloride
Compound 49: (1RS,2SR)-4-methyl-1-(3-methylphenyl)-2-(3-piperidinopropylamino)pentan-1-ol dihydrochloride
Compound 50: (1RS,2RS)-4-methyl-1-(3-methylphenyl)-2-(3-piperidinopropylamino)pentan-1-ol dihydrochloride
Compound 51: (1RS,2SR)-4-methyl-1-(4-methylphenyl)-2-(3-piperidinopropylamino)pentan-1-ol dihydrochloride
Compound 52: (1RS,2RS)-4-methyl-1-(4-methylphenyl)-2-(3-piperidinopropylamino)pentan-1-ol dihyrochloride Compound 53: (1RS,2SR)-1-(4-methoxyphenyl)-4-methyl-2-(3-piperidinopropylamino)pentan-1-ol dihydrochloride Compound 54: (1RS,2RS)-1-(4-methoxyphenyl)-4-methyl-2-(3-piperidinopropylamino)pentan-1-ol dihydrochloride Compound 55: (1RS,2SR)-1-(4-fluorophenyl)-4-methyl-2-(3-piperidinopropylamino)pentan-1-ol dihydrochloride Compound 56: (1RS,2RS)-1-(4-fluorophenyl)-4-methyl-2-(3-piperidinopropylamino)pentan-1-ol dihydrochloride Compound 57: (1RS,2SR)-1-(4-chlorophenyl)-4-methyl-2-(3-piperidinopropylamino)pentan-1-ol dihydrochloride Compound 58: (1RS,2RS)-1-(4-chlorophenyl)-4-methyl-2-(3-piperidinopropylamino)pentan-1-ol dihydrochloride Compound 59: (1RS,2SR)-5-methyl-1-phenyl-2-(3-piperidinopropylamino)hexan-1-ol methylether dihydrochloride Compound 60: (1RS,2RS)-5-methyl-1-phenyl-2-(3-piperidinopropylamino)hexan-1-ol methylether dihydrochloride Compound 61: (1RS,2SR)-5-methyl-1-phenyl-2-(3-piperidinopropylamino)hexan-1-ol ethylether dihydrochloride Compound 62: (1RS,2RS)-5-methyl-1-phenyl-2-(3-piperidinopropylamino)hexan-1-ol ethylether dihydrochloride Compound 63: (1RS,2SR)-2-[methyl-(3-piperidinopropyl)amino]-5-methyl-1-phenylhexan-1-ol dihydrochloride Compound 64: (1RS,2RS)-2-[methyl-(3-piperidinopropyl)amino]-5-methyl-1-phenylhexan-1-ol dihydrochloride Compound 65: (1RS,2SR)-2-[ethyl-(3-piperidinopropyl)amino]-5-methyl-1-phenylhexan-1-ol dihydrochloride Compound 66: (1RS,2RS)-2-[ethyl-(3-piperidinopropyl)amino]-5-methyl-1-phenylhexan-1-ol dihydrochloride The effectiveness of the compounds (I) according to the invention was determined with respect to the blocking effects against glutamic acid, the neuraxial muscle relaxing effects (the rigidity reducing and releasing effects on anemic decerebrate rigidity) and the toxicity levels. The following compounds were used for comparative purposes.

Comparative compound 1: (1RS,2SR)-1-phenyl-2-(2-piperidinoethylamino)propan-1-ol dihydrochloride Comparative compound 2: (1RS,2SR)-1-phenyl-2-(2-pyrrolidinoethylamino)propan-1-ol dihydrochloride Comparative compound 3: (1RS,2SR)-2-(2-morpholinoethylamino)-1-phenylpropan-1-ol dihydrochloride Comparative compound 4: (1RS,2SR)-2-(2-dimethylaminoethylamino)-1-phenylpropan-1-ol dihydrochloride Comparative compound 5: tolperisone hydrochloride

EXPERIMENT 1

Blocking Effects against Glutamic Acid at Neuromuscular Junctions of Crayfish

The method of Ishida et al. [J. Physiol., 298, 301-319 (1980)] and that of Shinozaki et al. [Comp. Biochem. Physio., 70c, 49-58 (1981)] followed. The opener muscles of the first walking legs of crayfish were used as experimental materials. The neuromuscular sample was held in a bath in which a physiological solution [composition (mM): NaCl (195), $CaCl_2$(18), KCl (5.4), trismaleate buffer (pH 7.5; 10), glucose (11)] for use with the crayfish was perfused at room temperature and at a constant flow rate. A glass micro-electrode filled with a 3M-KCl solution was inserted in a central part of the muscle fiber to intracellularly record changes in the potential of the muscular cell membrane.

The blocking effect of each test compound against glutamic acid was evaluated in terms of the suppression rate to depolarization which was induced by bath-applying L-glutamic acid ($10^{-4}$ M) in a 5-minute pretreatment with a solution of the test compound ($2 \times 10^{-4}$ M). The results are shown in Table 1.

TABLE 1

| Test compound | Blocking rate against glutamic acid (%) | Test compound | Blocking rate against glutamic acid (%) |
|---|---|---|---|
| Inventive compound | | Inventive compound | |
| 1 | 98 | 35 | 100 |
| 3 | 99 | 37 | 99 |
| 5 | 100 | 39 | 100 |
| 6 | 100 | 41 | 94 |
| 7 | 98 | 43 | 95 |
| 11 | 100 | 45 | 100 |
| 13 | 96 | 47 | 100 |
| 15 | 100 | 49 | 100 |
| 16 | 95 | 51 | 100 |
| 17 | 100 | 52 | 93 |
| 18 | 97 | 53 | 91 |
| 19 | 100 | 55 | 99 |
| 20 | 98 | 57 | 99 |
| 21 | 100 | 58 | 97 |
| 22 | 100 | 59 | 97 |
| 23 | 97 | 65 | 99 |
| | | Comparative compound | |
| 25 | 90 | 1 | 59 |
| 27 | 95 | 3 | 30 |
| 29 | 93 | 4 | 0-50 |
| 31 | 91 | | |

EXPERIMENT 2

Effects on Anemic Decerebrate Rigidity

An anemic decerebrate rigidity sample was prepared principally in accordance with the procedure of Fukuda et al. [Japan. J. Pharmacol., 24, 810 (1974)]. Wistar male rats (body weight: 270 to 350 g) were held on their backs and incised at their cervices under etherization. After the trachea and common carotid arteries were exposed, the trachea was cannulated and the bilateral common carotid arteries and esophagus were then double-ligated and cut. Thereafter, its occipital bone was exposed through which a circular hole was bored to double-ligate the centrally extending basilar artery. As each rat started coming out of anesthetization, its front limbs became rigid. Measurement was conducted by recording electromyographic (EMG) response from the muscle of the forelimb (M. triceps brachii) of the rat in the rigid state. The EMG pulses were converted to accumulated values every 10 seconds and recorded as a histogram on a recorder.

The effect of each test compound on the rigidity was evaluated in terms of the suppression rate. This rate was calculated first by determining the area of a decreased EMG pulse part on the histogram upon passage of 10 minutes after administration of a physiological saline solution of each test compound (3 mg/kg) through the femoral vein and then in accordance with the following equation.

$$\text{Suppression rate (\%)} = \frac{a}{A} \times 100$$

where
a: EMG pulse area decreased as a result of the administration of the test compound; and
A: EMG pulse area when no test compound was administered (control).

The results are shown in Table 2.

TABLE 2

| Test compound | Suppression rate (%) |
|---|---|
| Inventive compound | |
| 3 | 17.5 |
| 5 | 18.5 |
| 21 | 65.9 |
| 22 | 42.3 |
| 35 | 21.6 |
| 41 | 23.5 |
| 43 | 16.1 |
| 45 | 90.5 |
| Comparative compound | |
| 2 | 2.2 |
| 3 | 1.0 |
| 4 | 1.1 |
| 5 | 4.8 |

EXPERIMENT 3

Acute Toxicity

Using ddN male mice, the acute toxicity level of each test compound was determined in accordance with an up-and-down method. Some of the test compounds used were dissolved in physiological saline and administered through the caudal vein. The results are shown in Table 3.

TABLE 3

| Test compound | LD50 (mg/kg) (iv) |
|---|---|
| Inventive compound | |
| 3 | 19.2 |
| 5 | 22.1 |
| 15 | 23.6 |
| 16 | 28.8 |
| 17 | 15.4 |
| 19 | 28.4 |
| 21 | 13.6 |
| 22 | 19.0 |
| 35 | 26.7 |
| 41 | 29.5 |
| 43 | 31.9 |
| 45 | 12.8 |

The following specific examples and reference examples are given to further illustrate the present invention.

EXAMPLE 1

(1RS,2SR)-5-Methyl-1-phenyl-2-(3-piperidino-propylamino)hexan-1-ol dihydrochloride A mixture of (1RS,2SR)-2-amino-5-methyl-1-phenyl-hexan-1-ol (415 mg, 2 mmol) and 1-(3-chloropropyl)-piperidine (324 mg, 2 mmol) was melted at 70° C. in a nitrogen atmosphere. The mixture was heated at 110° to 120° C. for 3 hours. After being cooled, the reaction mixture was dissolved with heating in ethanol, followed by addition of concentrated hydrochloric acid (0.2 ml).

After the mixture was cooled, precipitated crystals were collected by filtration and washed with ethanol. The crystals were recrystallized from ethanol to obtain 0.27 g of the title compound as white crystals (yield: 33%).

mp: 266°–267° C. (dec)

IR$\nu_{max}^{KBr}$(cm$^{-1}$): 3290, 2945, 2650, 2550, 1590, 1445, 1285, 1130, 1090, 950, 735, 700 free base
IR$\nu_{max}^{neat}$(cm$^{-1}$): 3290, 2930, 2860, 2800, 1605, 1460, 1445, 1120, 1040, 695

NMR(CDCl$_3$)δ: 0.60–0.86(6H, m, CH(C$\underline{H}_3$)$_2$)
0.86–1.85(13H, m, C$\underline{H}_2$C$\underline{H}_2$C$\underline{H}$(CH$_3$)$_2$,

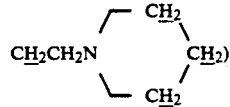
2.12–2.88(9H,
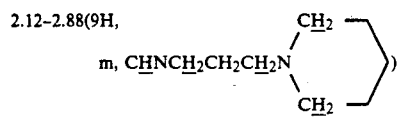
m, C$\underline{H}$NC$\underline{H}_2$CH$_2$C$\underline{H}_2$N ))

4.76(1H, d, J=4Hz, C$\underline{H}$—O)
7.24(5H, m, aromatic protons)

EXAMPLE 2

(1RS,2RS)-5-Methyl-1-phenyl-2-(3-piperidino-propylamino)hexan-1-ol dihydrochloride A mixture of (1RS,2RS)-2-amino-5-methyl-1-phenyl-hexan-1-ol (1.04 g, 5 mmol) and 1-(3-chloropropyl)-piperidine (0.81 g, 5 mmol) was melted at 70° C. in a nitrogen atmosphere. The mixture was then heated at 110° to 120° C. for 3 hours. After being cooled, the reaction mixture was dissolved with heating in ethanol, followed by addition of concentrated hydrochloric acid (0.5 ml). The resulting mixture was concentrated and the residue was crystallized by treatment with ethanol and hexane. The crystals were collected by filtration, washed with ethanol-hexane and then recrystallized from ethanol-hexane to obtain 1.24 g of the title compound as white crystals (yield: 61%).

mp 250°–251° C. (dec)

IR$\nu_{max}^{KBr}$(cm$^{-1}$): 3310, 2950, 2640, 1590, 1450, 1050, 760, 700 free base
IR$\nu_{max}^{neat}$(cm$^{-1}$): 3300, 2920, 2850, 2800, 1605, 1465, 1445, 1365, 1155, 1120, 1040, 755, 695

NMR(CDCl$_3$)δ: 0.68–0.92(6H, m, CH(C$\underline{H}_3$)$_2$)
0.92–1.81(13H, m, C$\underline{H}_2$C$\underline{H}_2$C$\underline{H}$(CH$_3$)$_2$,

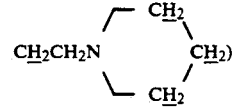
2.14–2.94(9H,
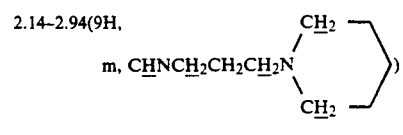
m, C$\underline{H}$NC$\underline{H}_2$CH$_2$C$\underline{H}_2$N ))

4.22(1H, d, J=8Hz, C$\underline{H}$—O)

-continued 7.24(5H, m, aromatic protons)

EXAMPLE 3

(1RS,2RS)-1-Phenyl-2-(3-piperidinopropylamino)octan-1-ol dihydrochloride

A mixture of (1RS,2RS)-2-amino-1-phenyloctan-1-ol (1.77 g, 8 mmol) and 1-(3-chloropropyl)piperidine (1.29 g, 8 mmol) was melted at 70° C. in a nitrogen atmosphere. The mixture was then heated at 110° to 120° C. for 3 hours. The reaction mixture was dissolved with heating in ethanol, followed by addition of concentrated hydrochloric acid (0.67 ml). Ethyl acetate was added and the resulting mixture was allowed to stand. Precipitated crystals were collected by filtration and washed with ethyl acetate and then with hexane to obtain 1.96 g of the title compound as white crystals (yield: 59%).

mp: 231°–234° C. (dec)

IR$\nu_{max}^{KBr}$(cm$^{-1}$): 3310, 2925, 2700, 1585, 1450, 1055, 760, 700
free base
IR$\nu_{max}^{neat}$(cm$^{-1}$): 3280, 2920, 2850, 2800, 1600, 1465, 1450, 1345, 1150, 1120, 1035, 755, 695
NMR(CDCl$_3$)δ: 0.68–1.02(3H, m, CH$_2$C$\underline{H}_3$)
1.02–1.09(20H, m, (C$\underline{H}_2$)$_5$CH$_3$,

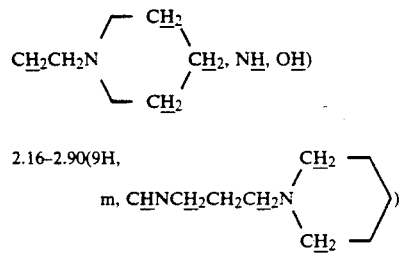

2.16–2.90(9H,
m, C$\underline{H}$NC$\underline{H}_2$CH$_2$C$\underline{H}_2$N 4.24(1H, d, J=8Hz, C$\underline{H}$—O)
7.30(5H, m, aromatic protons)

EXAMPLE 4

(1RS,2SR)-5-Methyl-1-phenyl-2-(2-piperidinoethyl)-hexan-1-ol dihydrochloride

A mixture of (1RS,2SR)-2-amino-5-methyl-1-phenyl-hexan-1-ol (1.04 g, 5 mmol) and 1-(2-chloroethyl)piperidine (0.74 g, 5 mmol) was melted at 70° C. in a nitrogen atmosphere. The mixture was then heated at 110° to 120° C. for 3 hours. After being cooled, the reaction mixture was dissolved in water. The solution was basified with 2N-NaOH and then extracted with ether. The ethereal extract was washed twice with water and once with brine, dried over anhydrous sodium sulfate and then evaporated under reduced pressure. The residue was dissolved in acetone (20 ml), followed by addition of concentrated hydrochloric acid (0.74 ml). Precipitated crystals were collected by filtration and washed with acetone. The crystals were recrystallized from ethanol (10 ml)-ether (2 ml) to obtain 0.34 g of the title compound as white crystals (yield: 17%).

mp: 223°–224° C. (dec)

IR$\nu_{max}^{KBr}$(cm$^{-1}$): 3260, 2950, 2700, 2470, 1600, 1450, 1200, 1050, 740, 700
free base
IR$\nu_{max}^{neat}$(cm$^{-1}$): 3180, 2940, 2860, 2820, 1600, 1445, 1250, 1105, 1050, 760, 695
NMR(CDCl$_3$)δ: 0.76(3H, d, J=6Hz, CHC$\underline{H}_3$)
0.79(3H, d, J=6Hz, CHC$\underline{H}_3$
1.00–1.77(11H, m, C$\underline{H}_2$C$\underline{H}_2$C$\underline{H}$(CH$_3$)$_2$,

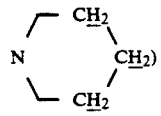

2.11–2.97(9H, m, C$\underline{H}$NC$\underline{H}_2$C$\underline{H}_2$N

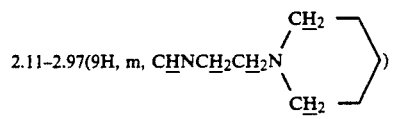

4.73(1H, d, J=4Hz, C$\underline{H}$—O)
7.30(5H, m, aromatic protons)

EXAMPLE 5

(1RS,2SR)-5-Methyl-1-phenyl-2-(3-piperidinopropylamino)hexan-1-ol dihydrochloride A mixture of (1RS,2SR)-2-amino-5-methyl-1-phenyl-hexan-1-ol (1.04 g, 5 mmol) and 1-(3-chloropropyl)-piperidine (0.81 g, 5 mmol) in benzene (10 ml) was refluxed for 40 hours. After being cooled, the reaction mixture was concentrated under reduced pressure. The residue was dissolved in ethanol (10 ml), followed by addition of 6N-HCl in EtOH (2 ml). Precipitated crystals were collected by filtration and then recrystallized from ethanol to obtain 1.15 g of the title compound as white crystals (yield: 57%).

mp 266°–267° C. (dec)

EXAMPLE 6

(1RS,2SR)-5-Methyl-1-phenyl-2-(3-piperidinopropylamino)hexan- 1-ol dihydrochloride A mixture of (1RS,2SR)-2-amino-5-methyl-1-phenyl-hexan-1-ol (1.04 g, 5 mmol), 3-piperidinopropyl tosylate hydrochloride (2.00 g, 6 mmol) and sodium bicarbonate (1.05 g, 12.5 mmol) in ethanol (10 ml) was refluxed for 1 hour. After cooling, to the reaction mixture were added ether (100 ml), water (50 ml) and 2N-NaOH (5 ml) and the resulting mixture was well shaken. The ethereal layer was separated and washed three times with water, then once with brine, followed by drying and subsequent concentration under reduced pressure. The residue was dissolved in ethanol and to the solution was added 6N-HCl in EtOH (1.5 ml). Precipitated crystals were collected by filtration and then recrystallized from ethanol to obtain 0.73 g of the title compound as white crystals (yield: 36%).

mp: 266°–267° C. (dec)

EXAMPLE 7

(1RS,2SR)-5-Methyl-1-phenyl-2-(3-piperidinopropylamino)hexan-1-ol methyl ether dihydrochloride To a solution of (1RS,2SR)-5-methyl-1-phenyl-2-(3-piperidinopropylamino)hexan-1-ol (1.66 g, 5 mmol) in toluene (25 ml) was added sodium hydride (0.14 g, 6 mmol) and the mixture was refluxed for 1 hour. To the reaction mixture was added methyl tosylate (1.12 g, 6 mmol) and the resulting mixture was refluxed for further 1 hour. After being cooled, the mixture was washed twice with water and once with brine, dried over anhydrous sodium sulfate and then concentrated under reduced pressure. The residue was purified by neutral alumina column chromatography (alumina: 40 g, eluent: chloroform) to give 1.1 g of oily matter. To a solution of the matter in acetone (20 ml) was added concentrated hydrochloric acid (0.1 ml) and the mixture was concentrated under reduced pressure. The residue was recrystallized from acetone (10 ml)-ethanol (0.2 ml) to obtain 0.45 g of the title compound as white crystals (yield: 21%).

mp: 138°–141° C.

---

IR$\nu_{max}^{KBr}$(cm$^{-1}$): 3360, 2940, 2640, 1570, 1450, 1120, 1095, 1060, 1010, 740, 695 free base

IR$\nu_{max}^{neat}$(cm$^{-1}$): 2940, 2860, 2810, 1460, 1445, 1150, 1120, 1100, 695

NMR(CDCl$_3$)δ: 0.70–0.96(6H, m, CH(C$\underline{H}_3$)$_2$)
1.00–1.70(14H, m, C$\underline{H}_2$)$_2$C$\underline{H}$(CH$_3$)$_2$,

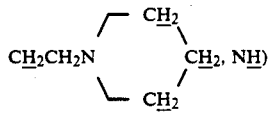, NH)

2.08–2.76(9H,

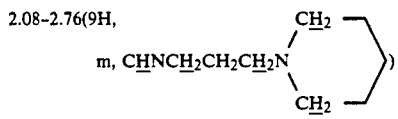)

3.24(3H, s, OCH$_3$)
4.17(1H, d, J=5Hz, C$\underline{H}$—O)
7.30(5H, m, aromatic protons)

---

EXAMPLE 8

(1RS,2SR)-2-[Ethyl-(3-piperidinopropyl)amino]-5-methyl-1-phenylhexan-1-ol dihydrochloride To a cooled mixture of (1RS,2SR)-5-methyl-1-phenyl-2-(3-piperidinopropylamino)hexan-1-ol (821 mg, 2.47 mmol) in ether (36 ml) and a 10% NaOH aqueous solution (15 ml) was added dropwise a solution of acetyl chloride (0.21 g, 2.7 mmol) in benzene. The organic layer was separated, washed with brine, dried over anhydrous sodium sulfate and then concentrated under reduced pressure. The residue was purified by silica gel column chromatography to obtain an N-acetylated product (IR$\nu_{max}^{neat}$: 1620 cm$^{-1}$) of the starting material. To a cooled solution of such compound in tetrahydrofuran (12.4 ml) was added lithium aluminum hydride (0.47 g) and the reaction mixture was refluxed for 3 hours. Ethyl acetate was added with cooling to the mixture to consume excess lithium aluminum hydride and the mixture was then poured into an aqueous saturated sodium sulfate solution. The organic layer was separated by decantation, dried over anhydrous sodium sulfate and concentrated under reduced pressure. The residue was purified by silica gel column chromatography (eluent: chloroform/methanol =25/1) to give a free base of the title compound. To a solution of the compound in ethanol was added in excess 6N-HCl in EtOH and the mixture was concentrated under reduced pressure. The residue was crystallized by treatment with ether, followed by recrystallization from ethanol-ethyl acetate to obtain 510 mg of the title compound as white crystals (yield: 48%).

mp: 190°–193° C.

---

IR$\nu_{max}^{KBr}$(cm$^{-1}$): 3400, 2950, 2870, 2660, 1450, 1420, 1090, 1050, 1030, 735, 700 free base

IR$\nu_{max}^{neat}$(cm$^{-1}$): 2940, 2870, 2820, 1490, 1465, 1445, 1380, 1365, 1345, 1155, 1125, 1065, 1040, 760, 700

NMR(CDCl$_3$)δ: 0.80(6H, d, J=6Hz, CH(C$\underline{H}_3$)$_2$)
1.02(3H, t, J=7Hz, NCH$_2$C$\underline{H}_3$)
1.10–1.82(13H, m, (C$\underline{H}_2$)$_2$C$\underline{H}$(CH$_3$)$_2$,

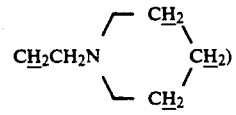)

1.90–2.94(11H,

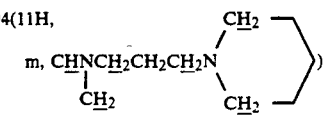)

4.76(1H, d, J=4Hz, C$\underline{H}$—O)
5.40(1H, broad s, O$\underline{H}$)
7.04–7.46(5H, m, aromatic protons)

---

EXAMPLE 9

(1RS,2RS)-5-Methyl-1-phenyl-2-(3-piperidinopropylamino)hexan-1-ol dihydrochloride A mixture of 2-bromo-5-methyl-1-phenylhexan-1-ol [prepared from 2-bromo-5-methyl-1-phenylhexan-1-one by usual NaBH$_4$-reduction] (1.0 g, 3.69 mmol) and 1-(3-aminopropyl)piperidine (1.05 g, 7.38 mmol) was heated at 110° C. for 4 hours in a nitrogen atmosphere. After being cooled, the reaction mixture was dissolved in 1N-HCl (50 ml) and the solution was washed with ether. The aqueous layer was basified with 1N-NaOH and then extracted twice with ether. The combined ethereal extract was washed three times with water, dried over anhydrous sodium sulfate and evaporated under reduced pressure. The residue was purified by preparative TLC to give pale yellow oily matter. To a solution of the matter in ethanol was added in excess 18% HCl in EtOH and the resulting mixture was evaporated under reduced pressure. The residue was dissolved with heating in ethanol (15 ml) and to the mixture was then added 10 ml of acetone. The mixture was stirred at room temperature. Precipitated crystals were collected by filtration to obtain 0.52 g of the title compound (yield: 35%).

mp: 250°–251° C. (dec)

EXAMPLE 10

(1RS,2SR)-5-Methyl-1-phenyl-2-(3-piperidinopropylamino)hexan-1-ol dihydrochloride To a solution of 1-(3-aminopropyl)piperidine (0.14 g, 1 mmol) in chloroform (2 ml) was added a solution of 2-bromo-5-methyl-1-phenylhexan-1-one [bp: 128°–130° C./2.5 mmHg; prepared from 5-methyl-1-phenylhexan-1-one by usual bromination] (0.54 g, 2 mmol) in chloroform (4 ml) and the mixture was stirred for 4 hours at room temperature in a nitrogen atmosphere. The reaction mixture was concentrated below 30° C. under reduced pressure. To a solution of the residue in methanol (4 ml) was added sodium borohydride (0.08 g) with ice-cooling and the mixture was stirred for 1 hour at room temperature. The reaction mixture was concentrated below 30° C. under reduced pressure. The residue was dissolved in 1N-HCl and the solution was washed twice with ethyl acetate, basified with 1N-NaOH and then extracted with ether. The ethereal extract was washed with water and then with brine, dried over anhydrous sodium sulfate and concentrated under reduced pressure to obtain 0.18 g of pale yellow oil. To a solution of the oil in ethanol (4 ml) was added 0.22 g of 18% HCl in EtOH and the mixture was allowed to stand overnight. Precipitated crystals were collected by filtration to obtain 0.11 g of the title compound as white crystals (yield: 27%).

mp: 266°–267° C. (dec)

EXAMPLE 11

(1RS,2SR)-5-Methyl-1-phenyl-2-(3-piperidinopropylamino)hexan-1-ol dihydrochloride To a refluxing mixture of 1-(3-aminopropyl)piperidine (284 mg, 2 mmol), sulfurous acid (6% $SO_2$ aqueous solution) (1.1 ml) and zinc dust (200 mg) in methanol (2.5 ml) was added dropwise over a period of 1 hour a solution of 5-methyl-1-phenylhexane-1,2-dione [bp: 104°–107° C./2 mmHg; prepared from 2-bromo-5-methyl-1-phenylhexan-1-one by a known method {N. Kornblum and H. W. Frazier: J. Am. Chem. Soc., 88, 865 (1966)}] (275 mg, 1.35 mmol) in methanol (1.0 ml). Thereafter, 200 mg of zinc dust and 1.8 ml of sulfurous acid were freshly added to the mixture and the resulting mixture was refluxed for further 2 hours. After cooling, methanol was added to the mixture and insoluble material was removed by filtration. The filtrate was concentrated under reduced pressure and the residue was dissolved in 2N-HCl. The resulting solution was washed three times with ether and then basified with an aqueous sodium hydroxide solution, followed by extraction with ether. The combined ethereal extract was washed twice with water, dried over anhydrous sodium sulfate and evaporated under reduced pressure to give 0.43 g of oily matter. To an ethanol solution of the matter was added 6N-HCl in EtOH (0.64 ml) and the solution was allowed to stand. Precipitated crystals were collected by filtration and washed with ethanol to obtain 170 mg of the title compound as white crystals (yield: 31%).

mp: 266°–267° C. (dec)

EXAMPLE 12

(1RS,2SR)-5-Methyl-1-phenyl-2-(3-piperidinopropylamino)hexan-1-ol dihydrochloride A mixture of 1-hydroxy-5-methyl-1-phenylhexan-2-one [bp: 111°–115° C./2 mmHg; prepared by a known method, e.g. D. H. Hey: J. Chem. Soc., 1232 (1930)] (413 mg, 2 mmol), 1-(3-aminopropyl)piperidine (285 mg, 2 mmol) and 0.4 g of 5% Pd/C in methanol (20 ml) was shaken in a shaker bomb at 4 atms of hydrogen for 16 hours at room temperature. The catalysts were removed by filtration and the filtrate was concentrated under reduced pressure. The residue was dissolved in ether and the solution was washed twice with water, dried and then evaporated under reduced pressure. The residue was dissolved in ethanol (12 ml) and to the solution was added 0.7 ml of 6N-HCl in EtOH. The resulting solution was allowed to stand. Precipitated crystals were collected by filtration to obtain 340 mg of the title compound (yield: 42%).

mp: 266°–267° C. (dec)

EXAMPLE 13

(1RS,2SR)-5-Methyl-1-phenyl-2-(3-piperidinopropylamino)hexan-1-ol dihydrochloride To a solution of 1-(3-aminopropyl)piperidine (285 mg, 2 mmol) in methanol (6 ml) was added 0.1 ml of 6.8N-HCl in MeOH, 1-hydroxy-5-methyl-1-phenylhexan-2-one (413 mg, 2 mmol) and sodium cyanoborohydride (126 mg, 2 mmol). The reaction mixture was stirred for 19 hours at room temperature. The mixture was concentrated under reduced pressure and to the residue was added 1N-HCl and ether. The aqueous layer was separated, basified with a 10% NaOH aqueous solution and then extracted three times with ether. The combined ethereal extract was washed twice with water, dried over anhydrous sodium sulfate and then evaporated under reduced pressure. The residue was dissolved in ethanol (12 ml). To the solution was added 0.70 ml of 6N-HCl in EtOH and the resulting mixture was allowed to stand. Precipitated crystals were collected by filtration to obtain 228 mg of the title compound (yield: 28%).

mp: 266°–267° C. (dec)

EXAMPLE 14

(1RS,2SR)-5-Methyl-1-phenyl-2-(3-piperidinopropylamino)hexan-1-ol dihydrochloride To a solution of sodium hydroxide (1.44 g) in water (6.6 ml) was added a solution of (4RS,5SR)-4-(3-methylbutyl)-5-phenyl-3-(3-piperidinopropyl)-1,3-oxazolidin-2-one (717 mg, 2 mmol) in ethanol (53 ml), the mixture was refluxed for 26 hours and then concentrated under reduced pressure. Water was added to the residue and the mixture was extracted three times with chloroform. The combined extract was dried over anhydrous sodium sulfate and then concentrated under reduced pressure. The residue was dissolved in ethanol (15 ml) and concentrated hydrochloric acid (0.34 ml) was added. Precipitated crystals were collected by filtration, washed first with ethanol and then with hexane to obtain 0.75 g of the title compound as white crystals (yield: 78%).

mp: 266°–267° C. (dec)

EXAMPLES 15-55

The compounds listed in Table 4-A were prepared in a similar manner as described in Examples 1 to 4 and the physical data of these compounds were shown in Table 4-B.

TABLE 4-A

Structure:

$$\text{Ph}(X)\text{-CH(OR}_4\text{)-CH(R}_1\text{)-N(R}_5\text{)-(CH}_2\text{)}_n\text{-N(R}_2\text{)(R}_3\text{)}$$

| Example | Configuration | $R_1$ | $N(R_2)(R_3)$ | $R_4$ | $R_5$ | X | n |
|---|---|---|---|---|---|---|---|
| 15 | 1RS, 2SR | —(CH$_2$)$_2$CH$_3$ | piperidin-1-yl | H | H | H | 3 |
| 16 | 1RS, 2RS | —(CH$_2$)$_2$CH$_3$ | piperidin-1-yl | H | H | H | 3 |
| 17 | 1RS, 2SR | —(CH$_2$)$_3$CH$_3$ | piperidin-1-yl | H | H | H | 3 |
| 18 | 1RS, 2RS | —(CH$_2$)$_3$CH$_3$ | piperidin-1-yl | H | H | H | 3 |
| 19 | 1RS, 2SR | —(CH$_2$)$_4$CH$_3$ | piperidin-1-yl | H | H | H | 3 |
| 20 | 1RS, 2RS | —(CH$_2$)$_4$CH$_3$ | piperidin-1-yl | H | H | H | 3 |
| 21 | 1RS, 2SR | —(CH$_2$)$_5$CH$_3$ | piperidin-1-yl | H | H | H | 3 |
| 22 | 1RS, 2SR | —CH(CH$_3$)$_2$ | piperidin-1-yl | H | H | H | 3 |
| 23 | 1RS, 2RS | —CH(CH$_3$)$_2$ | piperidin-1-yl | H | H | H | 3 |
| 24 | 1RS, 2SR | —CH$_2$CH(CH$_3$)$_2$ | piperidin-1-yl | H | H | H | 3 |
| 25 | 1RS, 2RS | —CH$_2$CH(CH$_3$)$_2$ | piperidin-1-yl | H | H | H | 3 |

TABLE 4-A-continued $$\text{Ar}\underset{\underset{X}{|}}{\bigcirc}\overset{OR_4}{\underset{R_1}{\text{CH}}}-\overset{R_5}{\underset{}{\text{CH}}}-\overset{}{\underset{}{\text{N}}}-(\text{CH}_2)_n-\overset{R_2}{\underset{R_3}{\text{N}}}$$

| Example | Configuration | R₁ | -N(R₂)(R₃) | R₄ | R₅ | X | n |
|---------|---------------|------|------|----|----|---|---|
| 26 | 1R, 2S | -CH₂CH(CH₃)₂ | piperidino | H | H | H | 3 |
| 27 | 1S, 2R | -CH₂CH(CH₃)₂ | piperidino | H | H | H | 3 |
| 28 | 1S, 2S | -CH₂CH(CH₃)₂ | piperidino | H | H | H | 3 |
| 29 | 1R, 2R | -CH₂CH(CH₃)₂ | piperidino | H | H | H | 3 |
| 30 | 1RS, 2SR | -CH₂CH(CH₃)₂ | piperidino | H | H | H | 3 |
| 31 | 1RS, 2RS | -CH₂CH(CH₃)₂ | piperidino | H | H | H | 3 |
| 32 | 1RS, 2SR | -CH₂CH(CH₃)₂ | morpholino | H | H | H | 3 |
| 33 | 1RS, 2RS | -CH₂CH(CH₃)₂ | morpholino | H | H | H | 3 |
| 34 | 1RS, 2SR | -CH₂CH(CH₃)₂ | -N(CH₃)₂ | H | H | H | 3 |
| 35 | 1RS, 2RS | -CH₂CH(CH₃)₂ | -N(CH₃)₂ | H | H | H | 3 |
| 36 | 1RS, 2SR | -CH₂CH(CH₃)₂ | piperidino | H | H | H | 2 |

TABLE 4-A-continued $$\text{structure with } OR_4, R_5, R_2, R_3, R_1, X, (CH_2)_n$$

| Example | Configuration | $R_1$ | $N(R_2)(R_3)$ | $R_4$ | $R_5$ | X | n |
|---------|---------------|-------|---------------|-------|-------|---|---|
| 37 | 1RS, 2RS | $-CH_2CH(CH_3)_2$ | piperidinyl | H | H | H | 2 |
| 38 | 1RS, 2SR | $-CH_2CH(CH_3)_2$ | piperidinyl | H | H | H | 2 |
| 39 | 1RS, 2RS | $-CH_2CH(CH_3)_2$ | piperidinyl | H | H | H | 2 |
| 40 | 1RS, 2SR | $-(CH_2)_2CH(CH_3)_2$ | piperidinyl | H | H | H | 3 |
| 41 | 1RS, 2SR | $-(CH_2)_2CH(CH_3)_2$ | morpholinyl | H | H | H | 3 |
| 42 | 1RS, 2SR | $-(CH_2)_2CH(CH_3)_2$ | $N(CH_3)_2$ | H | H | H | 3 |
| 43 | 1RS, 2SR | $-(CH_2)_2CH(CH_3)_2$ | piperidinyl | H | H | H | 2 |
| 44 | 1RS, 2SR | $-(CH_2)_2CH(CH_3)_2$ | azepanyl | H | H | H | 3 |
| 45 | 1RS, 2SR | $-CH_2CH(CH_3)_2$ | piperidinyl | H | H | 2-$CH_3$ | 3 |
| 46 | 1RS, 2SR | $-CH_2CH(CH_3)_2$ | piperidinyl | H | H | 3-$CH_3$ | 3 |
| 47 | 1RS, 2RS | $-CH_2CH(CH_3)_2$ | piperidinyl | H | H | 3-$CH_3$ | 3 |

TABLE 4-A-continued $$\underset{X}{\underset{|}{\bigcirc}}-\underset{R_1}{\underset{|}{CH}}-\underset{}{\underset{|}{CH}}-N-(CH_2)_n-N\underset{R_3}{\overset{R_2}{<}}$$
(with OR₄ on first CH and R₅ on second CH)

| Example | Configuration | R₁ | $-N\genfrac{}{}{0pt}{}{R_2}{R_3}$ | R₄ | R₅ | X | n |
|---|---|---|---|---|---|---|---|
| 48 | 1RS, 2SR | —CH₂CH(CH₃)₂ | piperidino | H | H | 4-CH₃ | 3 |
| 49 | 1RS, 2RS | —CH₂CH(CH₃)₂ | piperidino | H | H | 4-CH₃ | 3 |
| 50 | 1RS, 2SR | —CH₂CH(CH₃)₂ | piperidino | H | H | 4-OCH₃ | 3 |
| 51 | 1RS, 2SR | —CH₂CH(CH₃)₂ | piperidino | H | H | 4-F | 3 |
| 52 | 1RS, 2RS | —CH₂CH(CH₃)₂ | piperidino | H | H | 4-F | 3 |
| 53 | 1RS, 2SR | —CH₂CH(CH₃)₂ | piperidino | H | H | 4-Cl | 3 |
| 54 | 1RS, 2RS | —CH₂CH(CH₃)₂ | piperidino | H | H | 4-Cl | 3 |
| 55 | 1RS, 2SR | —(CH₂)₇CH₃ | piperidino | H | H | H | 3 |

TABLE 4-B

| Example | mp (dihydrochloride) | IR:$\nu_{max}^{KBr}$(cm⁻¹) (dihydrochloride) | NMR(δ:CDCl₃) (free base) or [α]_D (dihydrochloride) |
|---|---|---|---|
| 15 | 259–261° C. (dec) (EtOH) | 3300, 2940, 2775, 2550, 1585, 1445, 1285, 1085, 1045, 955, 730, 705 | 0.64–0.92(3H, m, CH₂C$\underline{H}$₃) 0.96–1.88(12H, m, (C$\underline{H}$₂)₂CH₃, 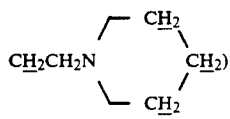 2.12–2.52(6H, m, 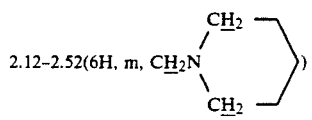 |

TABLE 4-B-continued

| Example | mp (dihydrochloride) | IR:$\nu_{max}^{KBr}$(cm$^{-1}$) (dihydrochloride) | NMR($\delta$:CDCl$_3$) (free base) or [$\alpha$]$_D$ (dihydrochloride) |
|---|---|---|---|
| 16 | 223–227° C. (dec) (EtOH—Et$_2$O) | 3325, 2930, 2680, 1590, 1450, 1050, 765, 700 | 2.56–2.88(3H, m, C$\underline{H}$NHC$\underline{H}_2$) 4.10(2H, broad S, N$\underline{H}$, O$\underline{H}$) 4.77(1H, d, J=4Hz, C$\underline{H}$—O) 7.29(5H, m, aromatic protons) 0.70–1.00(3H, m, CH$_2$C$\underline{H}_3$) 1.08–1.84(12H, m, (C$\underline{H}_2$)$_2$CH$_3$, 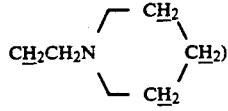 2.16–2.88(9H, m, C$\underline{H}$NHC$\underline{H}_2$CH$_2$C$\underline{H}_2$N 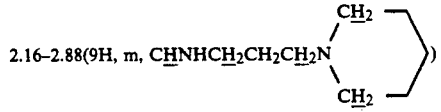) |
| 17 | 257–258° C. (dec) (MeOH) | 3280, 2940, 2650, 2550, 1590, 1440, 1280, 1090, 950, 720, 700 | 4.24(1H, d, J=8Hz, C$\underline{H}$—O) 7.31(5H, m, aromatic protons) 0.63–0.96(3H, m, CH$_2$C$\underline{H}_3$) 0.96–1.86(14H, m, (C$\underline{H}_2$)$_2$CH$_3$, 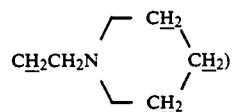 2.14–2.54(6H, m, C$\underline{H}_2$N 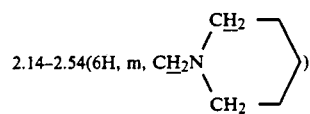) |
| 18 | 232–235° C. (dec) (EtOH—EtOAc) | 3290, 2930, 2640, 1585, 1445, 1040, 755, 695 | 2.54–2.91(3H, m, C$\underline{H}$NHC$\underline{H}_2$) 3.0–5.3(2H, broad S, N$\underline{H}$, O$\underline{H}$) 4.78(1H, d, J=4Hz, C$\underline{H}$—O) 7.30(5H, m, aromatic protons) 0.62–0.99(3H, m, CH$_2$C$\underline{H}_3$) 0.99–1.80(14H, m, (C$\underline{H}_2$)$_3$CH$_3$, 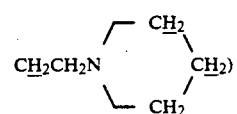 2.13–2.86(9H, m, C$\underline{H}$NHC$\underline{H}_2$CH$_2$C$\underline{H}_2$N ) |
| 19 | 261–262° C. (dec) (EtOH) | 3290, 2940, 2870, 2660, 2550, 1590, 1445, 1290, 1090, 950, 750, 720, 700 | 4.24(1H, d, J=8Hz, C$\underline{H}$—O) 7.30(5H, m, aromatic protons) 0.60–1.85(19H, m, (C$\underline{H}_2$)$_4$CH$_3$, 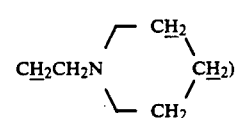 2.12–2.52(6H, m, C$\underline{H}_2$N 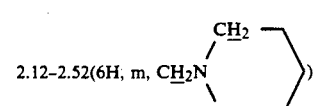) 2.52–2.87(3H, m, C$\underline{H}$NHC$\underline{H}_2$) 4.77(1H, d, J=4Hz, C$\underline{H}$—O) 7.29(5H, m, aromatic protons) |

TABLE 4-B-continued

| Example | mp (dihydrochloride) | IR:$\nu_{max}^{KBr}$(cm$^{-1}$) (dihydrochloride) | NMR($\delta$:CDCl$_3$) (free base) or $[\alpha]_D$ (dihydrochloride) |
|---|---|---|---|
| 20 | 238–241° C. (dec) (EtOH—EtOAc) | 3330, 2940, 2690, 2540, 1585, 1445, 1050, 760, 700 | 0.68–1.00(3H, m, CH$_2$C$\underline{H}_3$) 1.00–1.84(16H, m, (C$\underline{H}_2$)$_4$CH$_3$, CH$_2$CH$_2$N⟨CH$_2$-CH$_2$-CH$_2$⟩C$\underline{H}_2$) 2.12–2.86(9H, m, C$\underline{H}$NHC$\underline{H}_2$CH$_2$CH$_2$N⟨C$\underline{H}_2$-CH$_2$-CH$_2$-C$\underline{H}_2$⟩) 3.20(2H, broad S, O$\underline{H}$, N$\underline{H}$) 4.25(1H, d, J=8Hz, C$\underline{H}$—O) 7.30(5H, m, aromatic protons) |
| 21 | 253–255° C. (dec) (EtOH) | 3280, 2930, 2850, 2670, 2550, 1585, 1445, 1280, 1040, 955, 700 | 0.68–0.96(3H, m, CH$_2$C$\underline{H}_3$) 0.96–1.86(20H, m, (C$\underline{H}_2$)$_5$CH$_3$, CH$_2$CH$_2$N⟨C$\underline{H}_2$-CH$_2$-CH$_2$⟩C$\underline{H}_2$, N$\underline{H}$, O$\underline{H}$) 2.12–2.54(6H, m, C$\underline{H}_2$N⟨C$\underline{H}_2$-C$\underline{H}_2$⟩) 2.54–2.92(3H, m, C$\underline{H}$NHC$\underline{H}_2$) 4.78(1H, d, J=4Hz, C$\underline{H}$—O) 7.29(5H, m, aromatic protons) |
| 22 | 210–212° C. (dec) (EtOH) | 3290, 2940, 2670, 2555, 1600, 1445, 1285, 1125, 1060, 1000, 750, 700 | 0.87(6H, d, J=7Hz, CH(C$\underline{H}_3$)$_2$) 1.17–1.92(9H, m, C$\underline{H}$(CH$_3$)$_2$, CH$_2$CH$_2$N⟨C$\underline{H}_2$-CH$_2$-CH$_2$⟩C$\underline{H}_2$) 2.08–2.86(9H, m. C$\underline{H}$NHC$\underline{H}_2$CH$_2$CH$_2$N⟨C$\underline{H}_2$-CH$_2$-CH$_2$-C$\underline{H}_2$⟩) 4.77(1H, d, J=5Hz, C$\underline{H}$—O) 7.00–7.45(5H, m, aromatic protons) |
| 23 | 238–240° C. (dec) (EtOH) | 3270, 2930, 2650, 2520, 1585, 1450, 1020, 760, 700 | 0.92(3H, d, J=7Hz, CHC$\underline{H}_3$) 0.96(3H, d, J=7Hz, CHC$\underline{H}_3$) 1.17–1.95(9H, m, C$\underline{H}$(CH$_3$)$_2$, CH$_2$CH$_2$N⟨C$\underline{H}_2$-CH$_2$-CH$_2$⟩C$\underline{H}_2$) 2.04–2.89(9H, m, C$\underline{H}$NHC$\underline{H}_2$CH$_2$CH$_2$N⟨C$\underline{H}_2$-CH$_2$-CH$_2$-C$\underline{H}_2$⟩) 4.32(1H, d, J=6Hz, C$\underline{H}$—O) 7.00–7.45(5H, m, aromatic protons) |
| 24 | 268–270° C. (dec) (EtOH) | 3330, 2945, 2870, 2680, 2560, 1580, 1450, 1430, 1400, 1370, 1285, 1145, 1090, 1070, 1040, 965, 955, 755, 705 | 0.71(3H, d, J=6Hz, CHC$\underline{H}_3$) 0.82(3H, d, J=7Hz, CHC$\underline{H}_3$) 0.86–1.90(11H, m, C$\underline{H}_2$C$\underline{H}$(CH$_3$)$_2$ |

TABLE 4-B-continued

| Example | mp (dihydrochloride) | IR:$\nu_{max}^{KBr}$(cm$^{-1}$) (dihydrochloride) | NMR($\delta$:CDCl$_3$) (free base) or [$\alpha$]$_D$ (dihydrochloride) |
|---|---|---|---|
| 25 | 244–246° C. (dec) (EtOH—EtOAc) | 3360, 3030, 2940, 2870, 2680, 2550, 1575, 1480, 1450, 1430, 1410, 1385, 1365, 1285, 1080, 1070, 1050, 960, 950, 760, 700 | 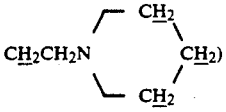 2.16–2.52(6H, m, CH$_2$N) 2.58–2.92(3H, m, CHNHCH$_2$) 4.10(2H, broad S, NH, OH) 4.80(1H, d, J=4Hz, CH—O) 7.29(5H, m, aromatic protons) 0.76(3H, d, J=6Hz, CHCH$_3$) 0.86(3H, d, J=6Hz, CHCH$_3$) 1.04–1.84(11H, m, CH$_2$CH(CH$_3$)$_2$, 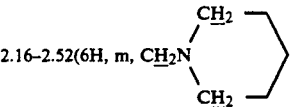 2.16–2.88(9H, m, CHNHCH$_2$CH$_2$CH$_2$N) |
| 26 | 266–267° C. (dec) (EtOH) | 3330, 2940, 2870, 2660, 2540, 1605, 1445, 1430, 1400, 1285, 1140, 1090, 1065, 1030, 960, 945, 745, 700 | 4.23(1H, d, J=7Hz, CH—O) 7.31(5H, m, aromatic protons) [$\alpha$]$_D$ −24.9°(C0.62, MeOH) |
| 27 | 266–267° C. (dec) (EtOH) | 3330, 2940, 2870, 2660, 2540, 1605, 1445, 1430, 1400, 1285, 1140, 1090, 1065, 1030, 960, 945, 745, 700 | [$\alpha$]$_D$ +25.3°(C0.60, MeOH) |
| 28 | 234–236° C. (dec) (EtOH—EtOAc) | 3300, 2950, 2700, 2550, 1570, 1450, 1430, 1390, 1370, 1280, 1200, 1140, 1080, 1045, 950, 760, 700 | [$\alpha$]$_D$ +24.3°(C0.60, MeOH) |
| 29 | 230–232° C. (dec) (EtOH—EtOAc) | 3300, 2950, 2700, 2550, 1570, 1450, 1430, 1390, 1370, 1280, 1200, 1140, 1080, 1045, 950, 760, 700 | [$\alpha$]$_D^{23}$ −24.3°(C0.60, MeOH) |
| 30 | 240–241° C. (dec) (EtOH) | 3320, 2950, 2680, 1595, 1445, 1090, 750, 695 | 0.71(3H, d, J=6Hz, CHCH$_3$) 0.82(3H, d, J=7Hz, CHCH$_3$) 0.88–1.96(9H, m, CH$_2$CH(CH$_3$)$_2$, 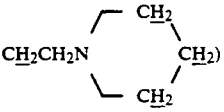 2.04–2.95(9H, m, CHNHCH$_2$CH$_2$CH$_2$N 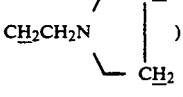) |
| 31 | 226.5–228.5° C. (dec) (EtOH—EtOAc) | 3280, 2960, 2685, 1580, 1450, 1040, 760, 695 | 3.13(2H, broad S, NH, OH) 4.82(1H, d, J=4Hz, CH—O) 7.29(5H, m, aromatic protons) 0.75(3H, d, J=6Hz, CHCH$_3$) 0.84(3H, d, J=6Hz, CHCH$_3$) 0.95–1.96(9H, m, CH$_2$CH(CH$_3$)$_2$, 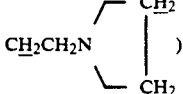 |

TABLE 4-B-continued

| Example | mp (dihydrochloride) | IR:$\nu_{max}^{KBr}$(cm$^{-1}$) (dihydrochloride) | NMR(δ:CDCl$_3$) (free base) or [α]$_D$ (dihydrochloride) |
|---|---|---|---|
| | | | 2.00–2.88(9H, m, C<u>H</u>NHC<u>H</u>$_2$CH$_2$CH$_2$N(CH$_2$/CH$_2$)) |
| 32 | 269–270° C. (dec) (EtOH) | 3275, 2940, 2665, 2600, 1590, 1440, 1255, 1110, 1090, 1045, 755, 705 | 3.17(2H, broad S, N<u>H</u>, O<u>H</u>) 4.24(1H, d, J=7Hz, C<u>H</u>—O) 7.30(5H, m, aromatic protons) 0.72(3H, d, J=6Hz, CHC2C<u>H</u>$_3$) 0.83(3H, d, J=6Hz, CHC<u>H</u>$_3$) 0.88–1.86(5H, m, C<u>H</u>$_2$C<u>H</u>(CH$_3$)$_2$, CH$_2$C<u>H</u>$_2$N(/O\)) 2.25–2.56(6H, m, C<u>H</u>$_2$N(CH$_2$/CH$_2$\O/)) 2.63–2.92(3H, m, C<u>H</u>NHC<u>H</u>$_2$) 3.0–4.6(2H, broad S, N<u>H</u>, O<u>H</u>) 3.69(4H, t, J=5Hz, N(CH$_2$\O/CH$_2$)) |
| 33 | 250–252° C. (dec) (EtOH) | 3300, 2950, 2600, 1580, 1450, 1260, 1110, 1085, 1040, 760, 700 | 4.79(1H, d, J=4Hz, C<u>H</u>—O) 7.29(5H, m, aromatic protons) 0.76(3H, d, J=6Hz, CHC<u>H</u>$_3$) 0.85(3H, d, J=6Hz, CHC<u>H</u>$_3$) 1.03–1.80(5H, m, C<u>H</u>$_2$C<u>H</u>(CH$_3$)$_2$, CH$_2$C<u>H</u>$_2$N(/O\)) 2.22–2.88(9H, m, C<u>H</u>NHC<u>H</u>$_2$CH$_2$CH$_2$N(CH$_2$/CH$_2$\O/)) 3.55–3.86(4H, m, N(CH$_2$\O/CH$_2$)) |
| 34 | 255–256° C. (dec) (EtOH-n-hexane) | 3300, 2960, 2760, 2645, 2510, 1590, 1455, 1430, 1105, 1065, 1045, 755, 700 | 4.24(1H, d, J=7Hz, C<u>H</u>—O) 2.4–6.4(2H, broad S, N<u>H</u>, O<u>H</u>) 7.30(5H, m, aromatic protons) 0.64–0.88(6H, m, CH(C<u>H</u>$_3$)$_2$) 0.88–2.88(12H, m, C<u>H</u>$_2$C<u>H</u>(CH$_3$)$_2$, C<u>H</u>NHC<u>H</u>$_2$CH$_2$CH$_2$N,N<u>H</u>, O<u>H</u>) 2.22(6H, S, N(C<u>H</u>$_3$)$_2$) |
| 35 | 243–244° C. (dec) (EtOH-n-hexane) | 3300, 2960, 2670, 1590, 1465, 1450, 1040, 760, 700 | 4.81(1H, d, J=4Hz, C<u>H</u>—O) 7.29(5H, m, aromatic protons) 0.68–0.96(6H, m, CH(C<u>H</u>$_3$)$_2$) 1.00–2.80(12H, m, C<u>H</u>$_2$C<u>H</u>(CH$_3$)$_2$, C<u>H</u>NHC<u>H</u>$_2$CH$_2$CH$_2$, N<u>H</u>, O<u>H</u>) 2.20(6H, S, N(C<u>H</u>$_3$)$_2$) |
| 36 | 234–235° C. (dec) (EtOH-n-hexane) | 3300, 2960, 2720, 2460, 1600, 1460, 1445, 750, 705 | 4.24(1H, d, J=7Hz, C<u>H</u>—O) 7.30(5H, m, aromatic protons) 0.64–0.88(6H, m, CH(C<u>H</u>$_3$)$_2$) 0.88–1.76(12H, m, |

TABLE 4-B-continued

| Example | mp (dihydrochloride) | IR: $\nu_{max}^{KBr}$(cm$^{-1}$) (dihydrochloride) | NMR(δ:CDCl$_3$) (free base) or [α]$_D$ (dihydrochloride) |
|---|---|---|---|
| | | | 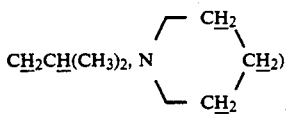<br>2.10–3.20(11H, m,<br>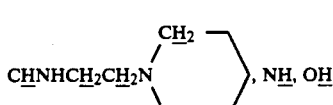, NH, OH) |
| 37 | 238–239° C. (dec) (EtOH-n-hexane) | 3270, 2955, 2720, 2480, 1560, 1550, 1445, 1385, 1055, 1010, 760, 690 | 4.75(1H, d, J=4Hz, CH—O)<br>7.29(5H, m, aromatic protons)<br>0.64–1.00(6H, m, CH(CH$_3$)$_2$)<br>1.00–1.76(9H, m,<br>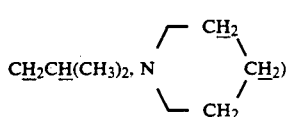)<br>2.10–2.90(9H, m,<br>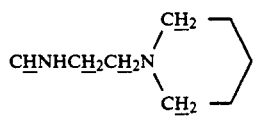) |
| 38 | 236–237° C. (dec) (EtOH) | 3290, 2960, 2650, 2460, 1595, 1460, 1445, 1090, 1025, 750, 705 | 3.34(2H, broad S, NH, OH)<br>4.24(1H, d, J=7Hz, CH—O)<br>7.30(5H, m, aromatic protons)<br>0.75(3H, d, J=7Hz, CHCH$_3$)<br>0.83(3H, d, J=7Hz, CHCH$_3$)<br>0.90–2.00(7H, m,<br>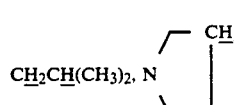)<br>2.10–3.00(9H, m,<br>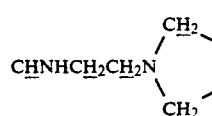) |
| 39 | 201–203° C. (acetone) | 3255, 2960, 2600, 1565, 1450, 1060, 1020, 765, 700 | 3.0–5.5(2H, broad S, NH, OH)<br>4.75(1H, d, J=4Hz, CH—O)<br>7.30(5H, m, aromatic protons)<br>0.75(3H, d, J=6Hz, CHCH$_3$)<br>0.84(3H, d, J=7Hz, CHCH$_3$)<br>0.93–2.00(7H, m,<br>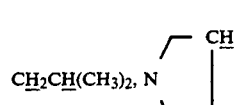)<br>2.10–2.90(9H, m,<br>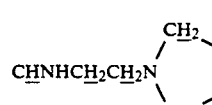) |

TABLE 4-B-continued

| Example | mp (dihydrochloride) | IR:$\nu_{max}^{KBr}$(cm$^{-1}$) (dihydrochloride) | NMR(δ:CDCl$_3$) (free base) or [α]$_D$ (dihydrochloride) |
|---|---|---|---|
| 40 | 253–253.5° C. (dec) (EtOH) | 3300, 2950, 2870, 2700, 1590, 1445, 1095, 1000, 740, 700 | 3.2–6.4(2H, broad S, N<u>H</u>, O<u>H</u>) 4.22(1H, d, J=7Hz, C<u>H</u>—O) 7.29(5H, m, aromatic protons) 0.76(3H, d, J=6Hz, CHC<u>H</u>$_3$) 0.77(3H, d, J=6Hz, CHC<u>H</u>$_3$) 0.96–2.05(11H, m, C<u>H</u>$_2$C<u>H</u>$_2$CH(CH$_3$)$_2$, C<u>H</u>$_2$CH$_2$N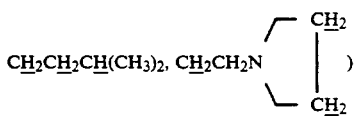) 2.24–2.93(9H, m, C<u>H</u>NHC<u>H</u>$_2$CH$_2$C<u>H</u>$_2$N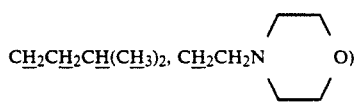) |
| 41 | 264.5–266.5° C. (dec) (EtOH) | 3280, 2940, 2870, 2670, 2590, 1590, 1435, 1255, 1110, 1095, 1050, 735, 700 | 4.78(1H, d, J=4Hz, C<u>H</u>—O) 7.30(5H, m, aromatic protons) 0.76(3H, d, J=6Hz, CHC<u>H</u>$_3$) 0.78(3H, d, J=6Hz, CHC<u>H</u>$_3$) 1.00–1.85(7H, m, C<u>H</u>$_2$C<u>H</u>$_2$CH(CH$_3$)$_2$, C<u>H</u>$_2$CH$_2$N O) 2.24–2.88(9H, m, C<u>H</u>NHC<u>H</u>$_2$CH$_2$C<u>H</u>$_2$N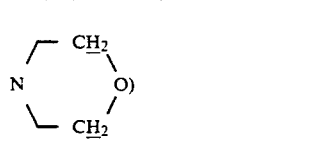O) 3.69(4H, t, J=5Hz, N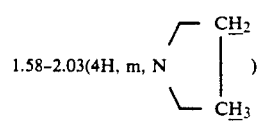O) |
| 42 | 248–249° C. (dec) (EtOH-c.HCl) | 3310, 2950, 2680, 2510, 1590, 1465, 1445, 1110, 1050, 1030, 740, 700 | 4.76(1H, d, J=4Hz, C<u>H</u>—O) 7.32(5H, m, aromatic protons) 0.75(3H, d, J=6Hz, CHC<u>H</u>$_3$) 0.77(3H, d, J=6Hz, CHC<u>H</u>$_3$) 0.96–1.90(7H, m, C<u>H</u>$_2$C<u>H</u>$_2$CH(CH$_3$)$_2$, C<u>H</u>$_2$CH$_2$N(CH$_3$)$_2$) 2.10–2.45(2H, m, C<u>H</u>$_2$N(CH$_3$)$_2$) 2.21(6H, S, N(C<u>H</u>$_3$)$_2$) 2.45–2.87(3H, m, C<u>H</u>NHC<u>H</u>$_2$) |
| 43 | 228–229° C. (dec) (EtOH-c.HCl) | 3320, 2960, 2870, 2680, 2600, 2480, 1580, 1445, 1350, 1095, 1020, 740, 700 | 4.77(1H, d, J=4Hz, C<u>H</u>—O) 7.29(5H, m, aromatic protons) 0.76(3H, d, J=6Hz, CHC<u>H</u>$_3$) 0.79(3H, d, J=6Hz, CHC<u>H</u>$_3$) C<u>H</u>$_2$C<u>H</u>$_2$CH(CH$_3$)$_2$) 1.58–2.03(4H, m, N<br>CH$_3$) 2.27–2.98(9H, m, |

TABLE 4-B-continued

| Example | mp (dihydrochloride) | IR:$\nu_{max}^{KBr}$(cm$^{-1}$) (dihydrochloride) | NMR(δ:CDCl$_3$) (free base) or [α]$_D$ (dihydrochloride) |
|---|---|---|---|
| 44 | 242.5–244° C. (dec) (EtOH) | 3330, 2940, 2880, 2720, 1590, 1450, 1100, 1050, 740, 700 | CH̲NHCH̲₂CH̲₂N(CH₂CH₂/CH₂CH₂) 4.74(1H, d, J=4Hz, CH̲—O) 7.30(5H, m, aromatic protons) 0.75(3H, d, J=6Hz, CHCH̲₃) 0.77(3H, d, J=6Hz, CHCH̲₃) 0.95–1.83(15H, m, CH̲₂CH̲₂CH(CH₃)₂, CH̲₂CH₂N(CH₂CH₂CH₂/CH₂CH₂)) 2.36–2.88(9H, m, CH̲NHCH̲₂CH₂CH̲₂N(CH₂CH₂/CH₂CH₂)) |
| 45 | 236–238° C. (dec) (isoPrOH—H₂O) | 3330, 2940, 2670, 2540, 1575, 1440, 1280, 1135, 1075, 1035, 950, 745 | 4.77(1H, d, J=4Hz, CH̲—O) 7.30(5H, m, aromatic protons) 0.64(3H, d, J=6Hz, CHCH̲₃) 0.79(3H, d, J=6Hz, CHCH̲₃) 0.86–1.88(11H, m, CH̲₂CH(CH₃)₂, CH̲₂CH₂N(CH₂/CH₂/CH₂)) 2.12–2.54(6H, m, CH̲₂N(CH₂/CH₂)) |
| 46 | 255–256° C. (dec) (90% EtOH) | 3280, 2930, 2680, 2540, 1600, 1440, 1075, 785, 755, 700 | 2.29(3H, S, CH₃-aryl) 2.54–3.04(3H, m, CHNHCH̲₂) 5.05(1H, d, J=3Hz, CH̲—O) 6.92–7.28, 7.40–7.64(4H, m, aromatic protons) 0.72(3H, d, J=6Hz, CHCH̲₃) 0.82(3H, d, J=6Hz, CHCH̲₃) 0.86–1.86(11H, m, CH̲₂CH(CH₃)₂, CH̲₂CH₂N(CH₂/CH₂/CH₂)) 2.08–2.56(6H, m, CH̲₂N(CH₂/CH₂)) |

TABLE 4-B-continued

| Example | mp (dihydrochloride) | IR:$\nu_{max}^{KBr}$(cm$^{-1}$) (dihydrochloride) | NMR($\delta$:CDCl$_3$) (free base) or $[\alpha]_D$ (dihydrochloride) |
|---|---|---|---|
| 47 | 240–243° C. (dec) (EtOH) | 3300, 2940, 2680, 2550, 1590, 1450, 1045, 780, 705 | 2.34(3H, S, 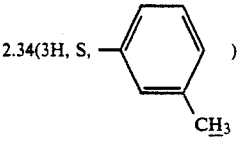) <br> 2.56–2.96(3H, m, CH̲NHCH̲$_2$) <br> 4.77(1H, d, J=4Hz, CH̲—O) <br> 6.84–7.34(4H, m, aromatic protons) <br> 0.77(3H, d, J=7Hz, CHCH̲$_3$) <br> 0.85(3H, d, J=7Hz, CHCH̲$_3$) <br> 1.02–1.76(11H, m, <br> CH̲$_2$CH̲(CH$_3$)$_2$, CH̲$_2$CH$_2$N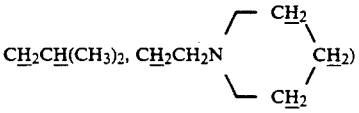) <br> 2.00–2.84(9H, m, <br> CH̲NHCH̲$_2$CH$_2$CH$_2$N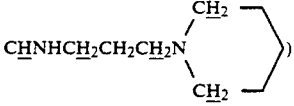) |
| 48 | 257–259° C. (dec) (EtOH—H$_2$O) | 3400, 3340, 2950, 2680, 1430, 1080, 850, 805, 760 | 2.33(3H, S, 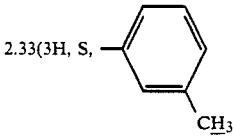) <br> 4.19(1H, d, J=7Hz, CH̲—O) <br> 6.88–7.28(4H, m, aromatic protons) <br> 0.72(3H, d, J=6Hz, CHCH̲$_3$) <br> 0.82(3H, d, J=6Hz, CHCH̲$_3$) <br> 0.88–1.84(11H, m, <br> CH̲$_2$CH̲(CH$_3$)$_2$, CH̲$_2$CH$_2$N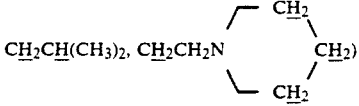) <br> 2.10–2.54(6H, m, <br> CH̲$_2$N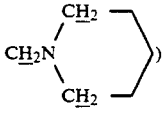) |
| 49 | 243–246° C. (dec) (EtOH) | 3420, 3300, 2940, 2860, 2740, 1605, 1570, 1445, 1425, 1045, 955, 810, 795 | 2.32(3H, S, 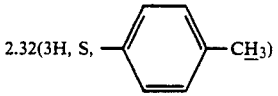—CH$_3$) <br> 2.56–2.90(3H, m, CH̲NHCH̲$_2$) <br> 4.76(1H, d, J=4Hz, CH̲—O) <br> 6.92–7.32(4H, m, aromatic protons) <br> 0.76(3H, d, J=7Hz, CHCH̲$_3$) <br> 0.83(3H, d, J=7Hz, CHCH̲$_3$) <br> 1.02–1.84(11H, m, <br> CH̲$_2$CH̲(CH$_3$)$_2$, CH̲$_2$CH$_2$N ) |

TABLE 4-B-continued

| Example | mp (dihydrochloride) | IR:$\nu_{max}^{KBr}$(cm$^{-1}$) (dihydrochloride) | NMR($\delta$:CDCl$_3$) (free base) or [$\alpha$]$_D$ (dihydrochloride) |
|---|---|---|---|
| | | | 2.07–2.88(9H, m, CHNHCH$_2$CH$_2$CH$_2$N(CH$_2$CH$_2$)$_2$) |
| | | | 2.31(3H, S, C$_6$H$_4$—CH$_3$) |
| 50 | 250–251° C. (dec) (90% EtOH) | 3370, 2930, 2680, 2540, 1605, 1505, 1440, 1250, 1170, 1075, 1030, 805 | 8.12(2H, broad S, OH, NH) 4.19(1H, d, J=7Hz, CH—O) 6.92–7.36(4H, m, aromatic protons) 0.73(3H, d, J=6Hz, CHCH$_3$) 0.83(3H, d, J=6Hz, CHCH$_3$) 0.86–1.84(11H, m, CH$_2$CH(CH$_3$)$_2$, CH$_2$CH$_2$N(CH$_2$CH$_2$)$_2$CH$_2$) |
| | | | 2.08–2.52(6H, m, CH$_2$N(CH$_2$CH$_2$)$_2$) |
| | | | 2.52–2.88(3H, m, CHNHCH$_2$) |
| | | | 3.79(3H, S, C$_6$H$_4$—OCH$_3$) |
| 51 | 275–276° C. (dec) (EtOH—H$_2$O) | 3400, 3260, 2960, 2680, 2550, 1605, 1505, 1465, 1450, 1430, 1390, 1370, 1285, 1230, 1160, 1140, 1080, 1040, 1010, 950, 830, 810, 785, 700 | 4.74(1H, d, J=4Hz, CH—O) 6.66–6.90, 7.02–7.32(4H, m, aromatic protons) 0.71(3H, d, J=6Hz, CHCH$_3$) 0.82(3H, d, J=6Hz, CHCH$_3$) 0.89–1.85(11H, m, CH$_2$CH(CH$_3$)$_2$, CH$_2$CH$_2$N(CH$_2$CH$_2$)$_2$CH$_2$) |
| | | | 2.12–2.57(6H, m, CH$_2$N(CH$_2$CH$_2$)$_2$) |
| 52 | 250–251° C. (dec) (EtOH) | 3300, 2940, 2870, 2640, 2550, 1605, 1585, 1450, 1230, 1155, 1050, 835 | 2.5–6.0(2H, broad S, OH, NH) 2.57–2.92(3H, m, CHNHCH$_2$) 4.77(1H, d, J=3Hz, CH—O) 6.80–7.44(4H, m, aromatic protons) 0.75(3H, d, J=6Hz, CHCH$_3$) 0.85(3H, d, J=6Hz, CHCH$_3$) 0.92–1.81(11H, m, |

TABLE 4-B-continued

| Example | mp (dihydrochloride) | IR:$\nu_{max}^{KBr}$(cm$^{-1}$) (dihydrochloride) | NMR($\delta$:CDCl$_3$) (free base) or $[\alpha]_D$ (dihydrochloride) |
|---|---|---|---|
| 53 | 278–279° C. (dec) (EtOH—H$_2$O) | 3400, 3260, 2940, 2880, 2680, 2550, 1600, 1470, 1445, 1390, 1370, 1140, 1085, 1040, 1015, 960, 850, 800 | 2.10–2.86(9H, m, 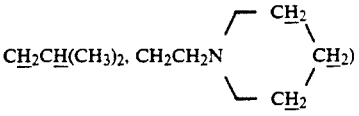 C$\underline{H}$NHC$\underline{H}_2$CH$_2$C$\underline{H}_2$N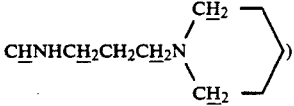) 4.20(1H, d, J=7Hz, C$\underline{H}$—O) 6.77–7.44(4H, m, aromatic protons) 0.71(3H, d, J=6Hz, CHC$\underline{H}_3$) 0.82(3H, d, J=6Hz, CHC$\underline{H}_3$) 0.84–1.84(11H, m, C$\underline{H}_2$C$\underline{H}$(CH$_3$)$_2$, C$\underline{H}_2$CH$_2$N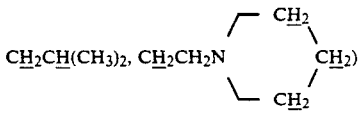) 2.08–2.54(6H, m, CH$_2$N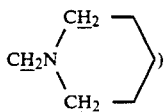) |
| 54 | 252–253° C. (dec) (EtOH) | 3400, 3230, 2950, 2700, 2560, 1600, 1580, 1475, 1450, 1430, 1390, 1370, 1200, 1140, 1090, 1060, 1015, 845, 815, 800 | 2.54–2.91(3H, m, C$\underline{H}$NHC$\underline{H}_2$) 4.77(1H, d, J=4Hz, C$\underline{H}$—O) 7.27(4H, m, aromatic protons) 0.76(3H, d, J=6Hz, CHC$\underline{H}_3$) 0.85(3H, d, J=6Hz, CHC$\underline{H}_3$) 0.95–1.77(11H, m, C$\underline{H}_2$C$\underline{H}$(CH$_3$)$_2$, C$\underline{H}_2$CH$_2$N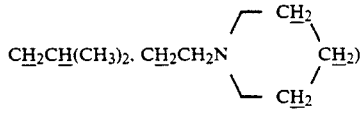) 2.10–2.82(9H, m, C$\underline{H}$NHC$\underline{H}_2$CH$_2$C$\underline{H}_2$N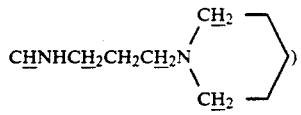) 4.20(1H, d, J=7Hz, C$\underline{H}$—O) 7.28(4H, m, aromatic protons) |
| 55 | 256–257° C. (dec) (EtOH) | 3300, 2930, 2860, 2680, 2550, 1600, 1445, 1400, 1350, 1285, 1200, 1135, 1090, 1065, 1010, 950, 700 | 0.68–0.98(3H, m, CH$_2$C$\underline{H}_3$) 0.98–1.84(22H, m, (C$\underline{H}_2$)$_7$CH$_3$, C$\underline{H}_2$CH$_2$N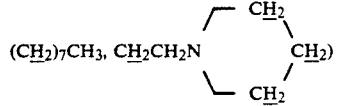) 2.12–2.53(6H, m, CH$_2$N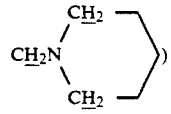) |

TABLE 4-B-continued

| Example | mp (dihydrochloride) | IR:$\nu_{max}^{KBr}$(cm$^{-1}$) (dihydrochloride) | NMR(δ:CDCl$_3$) (free base) or [α]$_D$ (dihydrochloride) |
|---------|----------------------|--------------------------------------------------|----------------------------------------------------------|
|         |                      |                                                  | 2.53–2.86(3H, m, CH̲NHCH̲$_2$)                           |
|         |                      |                                                  | 4.77(1H, d, J=4Hz, CH̲—O)                                |
|         |                      |                                                  | 7.29(5H, m, aromatic protons)                            |

REFERENCE EXAMPLE 1

2-(1,3-Dioxo-2-azaindan-2-yl)-4-methyl-1-phenylpentan-1-one

Thionyl chloride (34.8 ml, 480 mmol) was added to a mixture of 2-(1,3-dioxo-2-azaindan-2-yl)-4-methylpentanoic acid (83.61 g, 320 mmol) and benzene (320 ml). The resulting mixture was heated under reflux for 2 hours. The solvent and excess thionyl chloride were removed by distillation under reduced pressure, followed by addition of benzene (320 ml). The benzene was removed and fresh benzene (480 ml) was added to form a solution. Anhydrous aluminum chloride (106.7 g, 800 mmol) was added immediately to the solution and the mixture was stirred at room temperature for 3 hours. The reaction mixture was poured into ice-water (700 ml). The aqueous layer was extracted with benzene (200 ml). After being washed first with water and then with an aqueous sodium bicarbonate solution and with brine, the combined organic layer was dried over sodium sulfate and then evaporated under reduced pressure. The residue was treated with ethanol to give crystals. The crystals were dissolved with heating in ethanol (80 ml) and hexane (160 ml) was added. Precipitated crystals were collected by filtration and washed first with a 1:2 mixed solution (240 ml) of ethanol and hexane and then with hexane. The crystals were dried in air to obtain 74.6 g of the title compound as white crystals (yield: 73%).

REFERENCE EXAMPLE 2

(1RS,2SR)-2-(1,3-Dioxo-2-azaindan-2-yl)-4-methyl-1-phenylpentan-1-ol and (1RS,2RS)-2-(1,3-dioxo-2-azaindan-2-yl)-4-methyl-1-phenylpentan-1-ol Sodium cyanoborohydride (177 g, 2.82 mol) was added over 3 hours to a solution of the compound (141.4 g, 440 mmol) obtained in Reference Example 1 in chloroform (660 ml) and acetic acid (440 ml) while maintaining the reaction temperature below 30° C. The resulting mixture was stirred at room temperature for further 3 hours and then chloroform (1 liter) and water (1.4 liters) were added. The organic layer was separated and washed twice with water, once with an aqueous sodium bicarbonate solution and once with brine. After being dried over sodium sulfate, the organic layer was evaporated under reduced pressure to provide white crystals (142 g). The crystals were then charged on silica gel column chromatography (silica gel: 2.8 kg, solvent: benzene) to obtain first 94.3 g of the (1RS,2SR) isomer as white crystals (yield: 66%) and then 48.4 g of the (1RS,2RS) isomer as white crystals (yield: 34%).

REFERENCE EXAMPLE 3

(1RS,2RS)-2-(1,3-Dioxo-2-azaindan-2-yl)-4-methyl-1-phenylpentan-1-ol

Aluminum isopropoxide (125.6 g, 615 mmol) was added to a suspension of 2-(1,3-dioxo-2-azaindan-2-yl)-4-methyl-1-phenylpentan-1-one (72.3 g, 225 mmol) in isopropanol (1,000 ml). The mixture was heated under reflux for 6.5 hours. The isopropanol was removed by distillation under reduced pressure and to the residue were added ethyl acetate (800 ml) and an aqueous solution of sodium sulfate. The resulting organic layer was decanted and the residue was washed twice with ethyl acetate (200 ml). The combined organic layer was washed with brine. The organic solution was dried and the solvent was removed by distillation under reduced pressure. The residue was recrystallized twice from benzene to obtain 29.3 g of the title compound as white crystals (yield: 40%).

REFERENCE EXAMPLE 4

(1RS,2SR)-2-Amino-4-methyl-1-phenylpentan-1-ol (1RS,2SR)2-(1,3-Dioxo-2-azaindan-2-yl)-4-methyl-1-phenylpentan-1-ol (80.0 g, 247 mmol) was dissolved with heating (50° C.) in ethanol (800 ml), followed by addition of a mixture of 85% hydrazine hydrate (19.0 ml) in ethanol (200 ml). The resulting mixture was heated under reflux for 3 hours. After ice-cooling, 4N-HCl (700 ml) was added. The mixture was stirred at room temperature for 30 minutes. Insoluble matter was removed by filtration through celite and then washed with 4N-hydrochloric acid (140 ml). The washing was added to the filtrate and the solution was condensed under reduced pressure to remove the ethanol. A 6N-NaOH solution (570 ml) was added with ice-cooling and the mixture was extracted three times with chloroform. After being dried over sodium sulfate, the organic layer was evaporated to obtain 43.2 g of the title compound as white crystals (yield: 91%).

REFERENCE EXAMPLE 5

4-Methyl-1-(4-methylphenyl)-2-(1,3-dioxo-2-azaindan-2-yl)pentan-1-one

2-Bromo-4-methyl-1-(4-methylphenyl)pentan-1-one (13.5 g, 50 mmol) and potassium phthalimide (9.26 g, 50 mmol) were thoroughly mixed and heated at 160° C. for 2 hours. After cooling, to the reaction mixture were added ethyl acetate (100 ml) and water (50 ml). The resulting organic layer was separated and washed with brine. The organic solution was then dried over sodium sulfate and evaporated under reduced pressure. The residue was crystallized by treatment with hexane and the crystals were recrystallized from hexane to obtain 12.2 g of the title compound as white crystals (yield: 73%).

REFERENCE EXAMPLE 6

(1RS,2SR)-2-Amino-1-phenylheptan-1-ol

A mixture of potassium hydroxide(15 g) in water (150 ml) and 2-(1,3-dioxo-2-azaindan-2-yl)-1-phenylheptanone (20.1 g, 60 mmol) was refluxed for 30 minutes. After being cooled, the mixture was acidified with 5% hydrochloric acid. Precipitated white curd was separated by decantation. To the curd was added 225 ml of 5% hydrochloric acid and the mixture was refluxed for 1 hour and then allowed to stand overnight at room temperature. The white precipitate was removed by filtration and the filtrate was concentrated under reduced pressure. The remaining water was removed as an ethanol azeotrope. The residue was treated with hexane to give 14.5 g of 2-amino-1-phenylheptan-1-one hydrochloride (yield : 100%). To a cooled solution of the aminoketone hydrochloride (13.1 g) in methanol (130 ml) was added sodium borohydride (1.53 g, 40 mmol) in limited amounts so as to maintain the reaction temperature below 15 °C. Thereafter, the mixture was stirred at room temperature for 1 hour and concentrated under reduced pressure. To the residue was added chloroform and water. The mixture was basified with 2N-NaOH and the organic layer was separated. The aqueous layer was extracted twice with chloroform and the combined organic layer was washed with brine, dried over anhydrous sodium sulfate and then evaporated under reduced pressure. The residual white solid was recrystallized from hexane to obtain 7.95 g of the title compound as white crystals (yield : 71%).

REFERENCE EXAMPLE 7

(1RS,2RS)-2-Amino-1-phenylheptan-1-ol

Acetic anhydride (10 ml) was added to (1RS,2SR)-2-amino-1-phenylheptan-1-ol (4.15 g, 20 mmol) and the mixture was heated at 70° C. for 10 minutes. After being cooled, the reaction mixture was poured into water (100 ml) to which chloroform was added, followed by gradual addition of an aqueous sodium hydroxide solution. The solution thus basified was extracted with chloroform and the extract was dried. The solvent was removed by distillation under reduced pressure to obtain a colorless oil. The oil was ice-cooled, followed by addition of thionyl chloride (20 ml). The mixture was stirred at room temperature for 20 minutes. Water (30 ml) was added in limited amounts with caution and the mixture was heated under reflux for 2 hours. The mixture was cooled and then water was added. Subsequent to washing of the mixture with ether, the resulting aqueous layer was separated and basified with an aqueous sodium hydroxide solution. The mixture was extracted three times with chloroform and dried. The organic solution was evaporated under reduced pressure to give white crystals. The crystals were recrystallized from hexane to obtain 2.73 g of the title compound as white crystals (yield : 66%).

REFERENCE EXAMPLE 8

(1RS,2SR)-2-Amino-1-(4-methoxyphenyl)-4-methylpentan-1-ol

2-Hydroxyimino-1-(4-methoxyphenyl)-4-methylpentan-1-one (8.72 g, 37.1 mmol) was dissolved in acetic acid (88 ml). To the solution was added 5% palladium-charcoal (0.87 g) and the reactant was catalytically hydrogenated at normal pressure at 80° C. until hydrogen was absorbed in a molar amount of three times that of the reactant. After removal of the catalyst by filtration, the acetic acid was removed under reduced pressure. The residue was dissolved in 1N-HCl (80 ml). The solution was washed twice with ether (30 ml) and the aqueous layer was basified with a 20% aqueous solution of sodium hydroxide. The aqueous layer thus treated was extracted three times with chloroform and the extracts were combined together and then washed once with brine. The resulting extract was dried over sodium sulfate and the solvent was removed by distillation under reduced pressure to give light-yellowish crystals (6.80 g). The crystals were recrystallized from benzene and hexane to obtain 5.24 g of the title compound as white crystals (yield : 63%).

Amino alcohols useful as the starting materials for the compounds of the invention were synthesized by the combined use of the methods illustrated in Reference Examples (Method A : Reference Examples 1, 2 and 4, Method B : Reference Examples 1 and 6, Method C : Reference Example 7, Method D : Reference Example 8, Method E : Reference Examples 5, 3 and 4, Method F : Reference Examples 5, 2 and 4). The melting points and synthetic methods of the starting materials thus obtained are give in Table 5.

TABLE 5

$$\text{Ph}(X)-CH(OH)-CH(R_1)-NH_2$$

| X | $R_1$ | Configuration | mp and/or $[\alpha]_D$ | Synthetic method |
|---|---|---|---|---|
| H | $-(CH_2)_2CH_3$ | 1RS, 2SR | mp 66–66.5° C. | A |
| H | $-(CH_2)_2CH_3$ | 1RS, 2RS | mp 68.5–69° C. | A |
| H | $-(CH_2)_3CH_3$ | 1RS, 2SR | mp 72.5–74° C. | A |
| H | $-(CH_2)_3CH_3$ | 1RS, 2RS | mp 74–75° C. | A |
| H | $-(CH_2)_4CH_3$ | 1RS, 2SR | mp 67.5–68.5° C. | B |
| H | $-(CH_2)_4CH_3$ | 1RS, 2RS | mp 75–77° C. | C |
| H | $-(CH_2)_5CH_3$ | 1RS, 2SR | mp 79–80° C. | A |
| H | $-(CH_2)_5CH_3$ | 1RS, 2RS | mp 61–62° C. | A |
| H | $-(CH_2)_7CH_3$ | 1RS, 2SR | mp 77–78° C. | D |
| H | $-CH(CH_3)_2$ | 1RS, 2SR | mp 103–104.5° C. | A |
| H | $-CH(CH_3)_2$ | 1RS, 2RS | mp 60–62° C. | A |

TABLE 5-continued

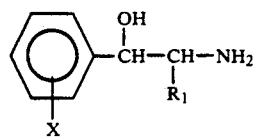

| X | R₁ | Configuration | mp and/or $[\alpha]_D$ | Synthetic method |
|---|---|---|---|---|
| H | —CH₂CH(CH₃)(CH₃) | 1RS, 2SR | mp 81–83° C. | A |
| H | —CH₂CH(CH₃)(CH₃) | 1RS, 2RS | mp 72–73° C. | A |
| H | —CH₂CH(CH₃)(CH₃) | 1R, 2S | mp 70–71° C. $[\alpha]_D^{23} -38.9°$ (c 1.0, EtOH) | A |
| H | —CH₂CH(CH₃)(CH₃) | 1S, 2R | mp 70–71° C. $[\alpha]_D^{23} +39.0°$ (c 1.0, EtOH) | A |
| H | —CH₂CH(CH₃)(CH₃) | 1S, 2S | mp 65–66° C. $[\alpha]_D^{23} -10.3°$ (c 1.0, EtOH) | A |
| H | —CH₂CH(CH₃)(CH₃) | 1R, 2R | mp 65–66° C. $[\alpha]_D^{23} +10.3°$ (c 1.0, EtOH) | A |
| H | —(CH₂)₂CH(CH₃)(CH₃) | 1RS, 2SR | mp 92–93° C. | A |
| H | —(CH₂)₂CH(CH₃)(CH₃) | 1RS, 2RS | mp 75–76° C. | A |
| 2-CH₃ | —CH₂CH(CH₃)(CH₃) | 1RS, 2SR | mp 64–65° C. | D |
| 3-CH₃ | —CH₂CH(CH₃)(CH₃) | 1RS, 2SR | mp 76–78° C. | D |
| 3-CH₃ | —CH₂CH(CH₃)(CH₃) | 1RS, 2RS | oil | C |
| 4-CH₃ | —CH₂CH(CH₃)(CH₃) | 1RS, 2SR | mp 75–76° C. | D |

TABLE 5-continued

Structure:

phenyl(X) — CH(OH) — CH(R₁) — NH₂

| X | R₁ | Configuration | mp and/or $[\alpha]_D$ | Synthetic method |
|---|---|---|---|---|
| 4-CH₃ | —CH₂CH(CH₃)₂ | 1RS, 2RS | mp 67.5–68.5° C. | E |
| 4-OCH₃ | —CH₂CH(CH₃)₂ | 1RS, 2SR | mp 80–82° C. | D |
| 4-F | —CH₂CH(CH₃)₂ | 1RS, 2SR | oil | D |
| 4-F | —CH₂CH(CH₃)₂ | 1RS, 2RS | oil | E |
| 4-Cl | —CH₂CH(CH₃)₂ | 1RS, 2SR | mp 95–97° C. | F |
| 4-Cl | —CH₂CH(CH₃)₂ | 1RS, 2RS | mp 68–71° C. | F |

REFERENCE EXAMPLE 9

(4RS,5SR)-4-(3-Methylbutyl)-5-phenyl-3-(3-piperidinopropyl)-1,3-oxazolidin-2-one A mixture of (4RS, 5SR)-4-(3-methylbutyl)-1,3-oxazolidin-2-one [mp: 111°–112 ° C.; prepared from (1RS,2SR)-2-amino-5-methyl-1-phenylhexan-1-ol by a known method {M. E. Dyen and D. Swern: Chem. Rev., 67, 197(1967)}] (1.17 g, 5 mmol), 1-(3-chloropropyl)piperidine hydrochloride (1.49 g, 7.5 mmol), anhydrous potassium carbonate powder (2.07 g, 15 mmol) in methyl ethyl ketone (15 ml) was refluxed with stirring for 24 hours. After cooling, insoluble material was removed by filtration and washed with methyl ethyl ketone. The washing and filtrate were combined together and concentrated under reduced pressure The residue was purified by silica gel column chromatography (silica gel:35 g ; eluent: chloroform/methanol) to obtain 1.52 g of the title compound as an oil (yield : 85%).

What is claimed is:

1. An amino-alcohol derivative of the formula (I),

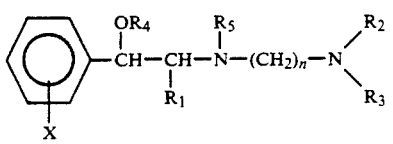

where R₁ is a straight or branched alkyl group having 3 to 8 carbon atoms, R₂ and R₃ are each a lower alkyl group, or R₂ and R₃ form a 5- to 7-membered ring together with the adjacent nitrogen atom which may have an oxygen atom attached thereto, R₄ is a hydrogen atom or a lower alkyl group, R₅ is a hydrogen atom or a lower alkyl group, X is a hydrogen or halogen atom or a lower alkyl or lower alkoxy group, and n is an integer of 2 or 3, or an acid addition salt thereof.

2. The amino-alcohol derivative of claim 1, wherein R₁ is a propyl group.

3. The amino-alcohol derivative of claim 1, wherein R₁ is a butyl group.

4. The amino-alcohol derivative of claim 1, wherein R₁ is a pentyl group.

5. The amino-alcohol derivative of claim 1, wherein R₁ is a hexyl group.

6. The amino-alcohol derivative of claim 1, wherein R₁ is an octyl group.

7. The amino-alcohol derivative of claim 1, wherein R₁ is an isopropyl group.

8. The amino-alcohol derivative of claim 1, wherein $R_1$ is an isobutyl group.

9. The amino-alcohol derivative of claim 1, wherein $R_1$ is an isopentyl group.

10. The amino-alcohol derivative of claim 1, wherein $R_2$ and $R_3$ taken together with the adjacent nitrogen atom form a 5- to 7-membered ring which may have an oxygen atom attached thereto.

11. The amino-alcohol derivative of claim 10, wherein $R_2$ and $R_3$ taken together with the adjacent nitrogen atom form a piperidinyl group.

12. The amino-alcohol derivative of claim 10, wherein $R_2$ and $R_3$ taken together with the adjacent nitrogen atom form a pyrrolidinyl group.

13. The amino-alcohol derivative of claim 10, wherein $R_2$ and $R_3$ taken together with the adjacent nitrogen atom form a morpholinyl group.

14. The amino-alcohol derivative of claim 10, wherein $R_2$ and $R_3$ taken together with the adjacent nitrogen atom form a perhydroazepin-1-yl group.

15. The amino-alcohol derivative of claim 11 which is the compound 5-methyl-1-phenyl-2-(3-piperidinopropylamino)hexan-1-ol.

16. The amino-alcohol derivative of claim 1, wherein X is a hydrogen atom.

17. The amino-alcohol derivative of claim 1, wherein X is a halogen atom.

18. The amino-alcohol derivative of claim 1, wherein X is a lower alkyl group.

19. The amino-alcohol derivative of claim 1, wherein X is a lower alkoxy group.

20. A method of treating spastic paralysis in a subject in need thereof, which comprises administering to the subject an effective amount of an amino-alcohol derivative of the formula I

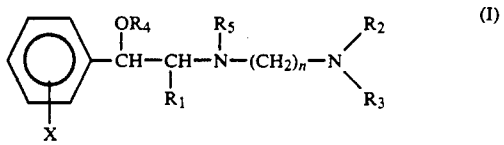

where $R_1$ is a straight of branched alkyl group having 3 to 8 carbon atoms, $R_2$ and $R_3$ are each a lower alkyl group, or $R_2$ and $R_3$ form a 5- or 7-membered ring together with the adjacent nitrogen atom which may have an oxygen atom attached thereto, $R_4$ is a hydrogen atom or a lower alkyl group, $R_5$ is a hydrogen atom or a lower alkyl group, X is a halogen atom or a lower alkyl group, and n is an integer of 2 or 3, or an acid addition salt thereof.

21. A method of treating spastic paralysis in a subject in need thereof, which comprises administering to the subject an effective amount of an amino-alcohol derivative of the formula I

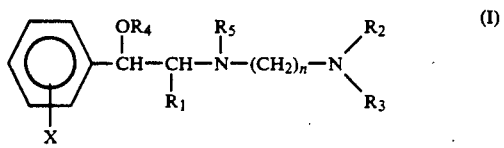

where $R_1$ is a straight or branched alkyl group having 3 to 8 carbon atoms, $R_2$ and $R_3$ are each a lower alkyl group, or $R_2$ and $R_3$ form a 5- or 7-membered ring together with the adjacent nitrogen atom which may have an oxygen atom attached thereto, $R_4$ is a hydrogen atom or a lower alkyl group, $R_5$ is a hydrogen atom or a lower alkyl group, X is a hydrogen or halogen atom or a lower alkyl or lower alkoxy group, and n is an integer of 2 or 3, or an acid addition salt thereof.

22. The method of treatment of claim 21, wherein $R_2$ and $R_3$ taken together with the adjacent nitrogen atom form a 5- to 7-membered ring which may have an oxygen atom attached thereto.

23. The method of treatment of claim 22 wherein $R_2$ and $R_3$ taken together with the adjacent nitrogen atom form a piperidinyl group.

24. The method of treatment of claim 22 wherein $R_2$ and $R_3$ taken together with the adjacent nitrogen atom form a pyrrolidinyl group.

25. The method of treatment of claim 22 wherein $R_2$ and $R_3$ taken together with the adjacent nitrogen atom form a morpholinyl group.

26. The method of treatment of claim 22 wherein $R_2$ and $R_3$ taken together with the adjacent nitrogen atom form a perhydroazepin-1-yl group.

27. The method of treatment of claim 21, wherein $R_1$ is a propyl group.

28. The method of treatment of claim 21, wherein $R_1$ is a butyl group.

29. The method of treatment of claim 21, wherein $R_1$ is a pentyl group.

30. The method of treatment of claim 21, wherein $R_1$ is a hexyl group.

31. The method of treatment of claim 21, wherein $R_1$ is an octyl group.

32. The method of treatment of claim 21, wherein $R_1$ is an isopropyl group.

33. The method of treatment of claim 21, wherein $R_1$ is an isobutyl group.

34. The method of treatment of claim 21, wherein $R_1$ is an isopentyl group.

35. The method of treatment of claim 20, wherein $R_2$ and $R_3$ taken together with the adjacent nitrogen atom form a 5- to 7-membered ring which may have an oxygen atom attached thereto.

36. The method of treatment of claim 35 wherein $R_2$ and $R_3$ taken together with the adjacent nitrogen atom form a piperidinyl group.

37. The method of treatment of claim 35 wherein $R_2$ and $R_3$ taken together with the adjacent nitrogen atom form a pyrrolidinyl group.

38. The method of treatment of claim 35 wherein $R_2$ and $R_3$ taken together with the adjacent nitrogen atom form a morpholinyl group.

39. The method of treatment of claim 35 wherein $R_2$ and $R_3$ taken together with the adjacent nitrogen atom form a perhydroazepin-1-yl group.

40. The method of treatment of claim 20, wherein $R_1$ is a propyl group.

41. The method of treatment of claim 20, wherein $R_1$ is a butyl group.

42. The method of treatment of claim 20, wherein $R_1$ is a pentyl group.

43. The method of treatment of claim 20, wherein $R_1$ is a hexyl group.

44. The method of treatment of claim 20, wherein $R_1$ is a octyl group.

45. The method of treatment of claim 20, wherein $R_1$ is a isopropyl group.

46. The method of treatment of claim 20, wherein $R_1$ is a isobutyl group.

47. The method of treatment of claim 20, wherein $R_1$ is a isopentyl group.

48. The method of treatment of claim 21, wherein the amino-alcohol derivative is the compound 5-methyl-1-phenyl-2-(3-piperidinopropylamino)hexan-1-ol.

* * * * *